United States Patent [19]

Hofstetter et al.

[11] Patent Number: 5,081,028
[45] Date of Patent: Jan. 14, 1992

[54] PREPARATION OF TRANSFORMED HOSTS WHICH EXPRESS BINDING FACTOR RELATED POLYPEPTIDES

[75] Inventors: Hans Hofstetter, Riehen; Erich Kilchherr, Gipf-Oberfrick, both of; Albert Schmitz, Basle, all of Switzerland

[73] Assignee: Ciba-Geigy Corporation, Ardsley, N.Y.

[21] Appl. No.: 617,487

[22] Filed: Nov. 21, 1990

Related U.S. Application Data

[63] Continuation of Ser. No. 73,788, Jul. 15, 1987, abandoned.

[30] Foreign Application Priority Data

Jul. 22, 1986 [GB] United Kingdom ............... 8617862
Nov. 7, 1986 [GB] United Kingdom ............... 8626622

[51] Int. Cl.[5] .................. C12N 15/00; C12N 5/16; C12N 1/21; C12N 1/19
[52] U.S. Cl. .................. 435/172.3; 435/252.3; 435/252.33; 435/240.2; 435/695; 930/140; 935/11; 935/28; 935/29; 935/32; 935/69; 935/70; 935/73
[58] Field of Search .................. 435/252.7, 172.3

[56] References Cited

U.S. PATENT DOCUMENTS

| | | | |
|---|---|---|---|
| 4,349,629 | 9/1982 | Carey | 435/172 |
| 4,666,847 | 5/1987 | Alford | 435/253 |
| 4,740,461 | 4/1988 | Kaufman | 435/68 |
| 4,757,021 | 7/1988 | Kawabe | 435/256 |
| 4,758,511 | 7/1988 | Marters | 435/68 |

FOREIGN PATENT DOCUMENTS

| | | |
|---|---|---|
| 155192 | 9/1985 | European Pat. Off. |
| 0205405 | 12/1986 | European Pat. Off. |
| 248211 | 12/1987 | European Pat. Off. |
| 257114 | 3/1988 | European Pat. Off. |
| 258489 | 3/1988 | European Pat. Off. |
| 258492 | 3/1988 | European Pat. Off. |
| 259615 | 3/1988 | European Pat. Off. |
| 8606407 | 11/1986 | PCT Int'l Appl. |
| WO8803172 | 5/1988 | PCT Int'l Appl. |

OTHER PUBLICATIONS

Suemura et al., Aug. 15, 1986, J. Immunol. 137:1214-1220.
Peterson, L. M. and Condrad D. H. Oct. 1985, J. Immunol. 135: 2654-2660.
Noro N. et al., Aug. 15, 1986, J. Immunol. 137: 1258-1263.
Kemp D. J. and Conman A. F. 1981 PNAS, U.S.A. 78(7) 4520-4524.
Skallca A. and Shapiro L. 1976 Gene 1:65-79.
Sarfati M. et al., 1984 Immunology 53:197-205.
Nakajima T. and Delespess G. 1986 Eur. S. Immunol 16: 809-874.
Rector E. et al., 1985 Immunology 55:481-488.
Maniatis et al., Molecular Cloning (1982).
Gary Buell et al., Nucleic Acids Research, 13, #6, pp. 1923-1937, (1985).
K. Ishizaka, Ann. Rev. Immunol. vol. 2, pp. 159-182 (1984).
Sarfati et al., J. Immunology vol. 53, pp. 197-205 (1984).
Sarfati et al., J. Immunology vol. 53, pp. 207-214 (1984).
Sarfati et al., J. Immunology vol. 53 pp. 783-790 (1984).
Huff et al., Proc. Natl. Acad. Sci. vol. 81 pp. 1514-1518 (1984).
Liu et al., Proc. Natl. Acad. Sci. vol. 82, pp. 4100-4104 (1985).

(List continued on next page.)

Primary Examiner—Richard A. Schwartz
Assistant Examiner—John L. LeGuyader
Attorney, Agent, or Firm—JoAnn Villamizar

[57] ABSTRACT

The invention concerns polypeptides related to human immunoglobulin E binding factors (IgE-Bfs), mRNa, DNAs and hybrid vectors coding for said polypeptides, hosts containing said hydrid vectors, processes for the preparation of said polypepties, mRNAs, DNAs, hybrid vectors, and hosts. The polypeptides can be used for the prevention and/or the treatment of allergic diseases, and accordingly the invention concerns also pharmaceutical preparations containing them.

15 Claims, 13 Drawing Sheets

FIGURE 9: Formula (I)

OTHER PUBLICATIONS

Kikutani et al., *Cell* vol. 47, pp. 657–665 (1986).
Ikuta et al., *Proc. Natl. Acad. Sci.* vol. 84, pp. 819–823 (1987).
Abstract of Japanese 62045600A (1985).
Lüdin et al., *The EMBO Journal*, vol. 6, No. 1, pp. 109–114 (1987).
*The EMBO Journal* vol. 1, No. 4, pp. 433–437 (1982), R. Everett et al.
D. Shortle et al., *Ann. Rev. Genet.* 1981, 15:265–294.
"Targeted Deletieens of Sequences from Closed Circular DNA", PNAS vol. 77, pp. 2455–2499 (1980).
S. Gillam and M. Smith, Gene 8 (1979) pp. 81–97.
Shortle et al., *PNAS* 791, pp. 1588–1592 (1982).
M. J. Zoller and M. Smith, *Nucleic Acids* Research, 10 (20) (1982).
*Nature*, vol. 299 (9/82) pp. 298–299.
Derwent Abstract of Japanese J6-2045-597A (1987).
Martens et al., *Proc. Natl. Acad. Sci. U.S.A.* vol. 82, pp. 2460–2464 (1985).
Okayama et al., Molecular & Cellular Biology pp. 161–170, 2 (1982).
Gisela Heidecker, Nucleic Acids Research, 11, #14, pp. 4891–4906 (1983).
Scarpulla et al., Analytical Biochemtry 121, pp. 356–365 (1982).
K. L. Agarwal et al., Angewoandte Chemie, 84, pp. 489–556 (1972).
Colin B. Reese, Tetrahedrom 34, 3143 (1972).
Robert L. Letsinger et al., J. Amer. Soc. 98, 3655 (1976).
H. Gobind Khorana et al., J. of Biological Chemistry, 251 No. 3, pp. 565–570 (1976).
Saran R. Narang, Tetrahedron 39, 3 (1983).
Chang et al., Nature 275 617–624 (1978).
David V. Goeddel et al., Nature 281, 544–548 (1979).
David V. Goeddel et al., Nucleic–Acids Research 8 p. 4057 (1980).
Ulrich Subenlist et al., Cell. vol. 20 pp. 269–281 (1980).
T. Stinchcomb et al., Nature 282, pp. 439–443 (1979).
A. J. Kingsman et al., Gene, 7, pp. 141–152, (1979).
G. Tschumper et al., Gene, 10, pp. 157–166 (1980).
D. A. Melton et al., Nucleis Acids Research, 12, #18, pp. 7035–7056 (1984).
F. C. Greenwood et al., Biochem. J. 89, pp. 114–123 (1963).
Brian Seed, Nucleic Acids Research, 10, #5, pp. 1799–1810 (1982).
F. Sanger et al., Proc. Natl, Sci. U.S.A. 74, #12, pp. 5463–5467 (1977).

FIGURE 9: Formula (I)

```
1               10                  20                  30
M E E G Q Y S E I E E L P R R R C C R R G T Q I V L L G L V
                40                  50                  60
T A A L W A G L L T L L L W H W D T T Q S L K Q L E E R A
                70                  80                  90
A R N V S Q V S K N L E S H H G D Q M A Q K S Q S T Q I S Q
                100                 110                 120
E L E E L R A E Q Q R L K S Q D L E L S W N L N G L Q A D L
                130                 140                 150
S S F K S Q E L N E R N E A S D L L E R L R E E V T K L R M
                160                 170                 180
E L Q V S S G F V C N T C P E K W I N F Q R K C Y Y F G K G
                190                 200                 210
T K Q W V H A R Y A C D D M E G Q L V S I H S P E E Q D F L
                220                 230                 240
T K H A S H T G S W I G L R N L D L K G E F I W V D G S H V
                250                 260                 270
D Y S N W A P G E P T S R S Q G E D C V M M R G S G R W N D
                280                 290                 300
A F C D R K L G A W V C D R L A T C T P P A S E G S A E S M
                310                 320
G P D S R P D P D G R L P T P S A P L H S
                                        321
```

FIGURE 10: Formula (II)

```
                                  AATCGCTCTGGTC GACCCCAACACA
                                              G
                             -145 -140        -130
CTAGGAGGACAGACACAGGCTCCAAACTCCACTAACCAGAGCTGTGATTGTGCCCGCTGA
-120    -110    -100    -90    -80    -70
GTGGACTGCGTTGTCAGGGAGTGAGTGCTCCATCATCGGGAGAATCCAAGCAGGACCGCC
-60     -50    -40    -30    -20    -10    -1

1                                                   20
   M   E   E   G   Q   Y   S   E   I   E   E   L   P   R   R   R   C   C   R   R
ATGGAGGAAGGTCAATATTCAGAGATCGAGGAGCTTCCCAGGAGGCGGTGTTGCAGGCGT
1       10      20      30      40      50      60

30                                40
   G   T   Q   I   V   L   L   G   L   V   T   A   A   L   W   A   G   L   L   T
GGGACTCAGATCGTGCTGCTGGGGCTGGTGACCGCCG TCTGTGGGCTGGGCTGCTGACT
                                     G
        70      80      90      100     110     120

50                                60
   L   L   L   L   W   H   W   D   T   T   Q   S   L   K   Q   L   E   E   R   A
CTGCTTCTCCTGTGGCACTGGGACACCACACAGAGTCTAAAACAGCTGGAAGAGAGGGCT
        130     140     150     160     170     180

70                            80
   A   R   N   V   S   Q   V   S   K   N   L   E   S   H   H   G   D   Q   M   A
GCCCGGAACGTCTCTCAAGTTTCCAAGAACTTGGAAAGCCACCACGGTGACCAGATGGCG
        190     200     210     220     230     240

90                            100
   Q   K   S   Q   S   T   Q   I   S   Q   E   L   E   E   L   R   A   E   Q   Q
CAGAAATCCCAGTCCACGCAGATTTCACAGGAACTGGAGGAACTTCGAGCTGAACAGCAG
        250     260     270     280     290     300

110                           120
   R   L   K   S   Q   D   L   E   L   S   W   N   L   N   G   L   Q   A   D   L
AGATTGAAATCTCAGGACTTGGAGCTGTCCTGGAACCTGAACGGGCTTCAAGCA GATCTG
                                                       G
        310     320     330     340     350     360

130                           140
   S   S   F   K   S   Q   E   L   N   E   R   N   E   A   S   D   L   L   E   R
AGCAGCTTCAAGTCCCAGGAATTGAACGAGAGGAACGAA GCTTCAGATTTGCTGGAAAGA
                                        H
        370     380     390     400     410     420

150                           160
   L   R   E   E   V   T   K   L   R   M   E   L   Q   V   S   S   G   F   V   C
CTCCGGGAGGAGGTGACAAAGCTAAGGATGGAGTTGCAGGTGTCCAGCGGCTTTGTGTGC
        430     440     450     460     470     480

170                           180
   N   T   C   P   E   K   W   I   N   F   Q   R   K   C   Y   Y   F   G   K   G
AACACGTGCCCTGAAAAGTGGATCAACTTCCAACGGAAGTGCTACTACTTCGGCAAGGGC
        490     500     510     520     530     540
                                                        (continued)
```

FIGURE 10 (continued)

```
             190                              200
 T   K   Q   W   V   H   A   R   Y   A   C   D   D   M   E   G   Q   L   V   S
ACCAAGCAGTGGGTCCACGCCCGGTATGCCTGTGACGACATGGAAGGGCAGCTGGTCAGC
    550       560       570       580       590       600

210                              220
 I   H   S   P   E   E   Q   D   F   L   T   K   H   A   S   H   T   G   S   W
ATCCACAGCCCGGAGGAGCAGGACTTCCTGACCAAGCATGCCAGCCACACCGGCTCCTGG
    610       620       630       640       650       660

230                              240
 I   G   L   R   N   L   D   L   K   G   E   F   I   W   V   D   G   S   H   V
ATTGGCCTTCGGAACTTGGACCTGAAGGGAGAGTTTATCTGGGTGGATGGGAGCCATGTG
    670       680       690       700       710       720

250                              260
 D   Y   S   N   W   A   P   G   E   P   T   S   R   S   Q   G   E   D   C   V
GACTACAGCAACTGGGCTCCAGGGGAGCCCACCAGCCGGAGCCAGGGCGAGGACTGCGTG
    730       740       750       760       770       780

270                              280
 M   M   R   G   S   G   R   W   N   D   A   F   C   D   R   K   L   G   A   W
ATGATGCGGGGCTCCGGTCGCTGGAACGACGCCTTCTGCGACCGTAAGCTGGGCGCCTGG
    790       800       810       820       830       840

290                              300
 V   C   D   R   L   A   T   C   T   P   P   A   S   E   G   S   A   E   S   M
GTGTGCGACCGGCTGGCCACATGCACGCCGCCAGCCAGCGAAGGTTCCGCGGAGTCCATG
    850       860       870       880       890       900

310                              320
 G   P   D   S   R   P   D   P   D   G   R   L   P   T   P   S   A   P   L   H
GGACCTGATTCAAGACCAGACCCTGACGGCCGCCTGCCCACCCCCTCTGCCCCTCTCCAC
    910       920       930       940       950       960

S
TCTTGAGCATGGATACAGCCAGGCCCAGAGCAAGACCCTGAAGACCCCCAACCACGGCCT
    970       980       990      1000      1010      1020

AAAAGCCTCTTTGTGGCTGAAAGGTCCCTGTGACATTTTCTGCCACCCAAACGGAGGCAG
   1030      1040      1050      1060      1070      1080

CTGACACATCTCCCGCTCCTCTATGGCCCCTGCCTTCCCAGGAGT↓ACACCCCAACAGCAC
   1090      1100      1110      1120      R 1130      1140

CCTCTCCAGATGGGAGTGCCCCCAACAGCACCCTCTCCAGATGAGAGT↓ACACCCCAACAG
   1150      1160      1170      1180      1190      1200
                                            R

CACCCTCTCCAGATGCAGCCCCATCTCCTCAGCACCCCAGGACCTGAGTATCCCCAGCTC
   1210      1220      1230      1240      1250      1260

AGGGTGGTGAGTCCTCCTGTCCAGCCTGCATCAATAAAATGGGGCAGTGATGGCC
   1270      1280      1290      1300      1310 1315
```

FIGURE 11: Formula (III)

```
            CTAACCACGCTAGTGAGTCAGATTGTAGACTAAACAAAATCAGCCAA
           -227    -220    -210    -200    -190

ATCGGCCCCTGAGTGCCACCAAGTCCCAGATGCTATCCTGTCCTGGTAACTAGGGTTTGA
-180    -170    -160    -150    -140    -130

TGGCTCACCCTAACCATCATTAAATTCCAAATCAGCCAGAGCTGTGATTGTGCCCGCTGA
-120    -110    -100    -90     -80     -70

GTGGACTGCGTTGTCAGGGAGTGAGTGCTCCATCATCGGGAGAATCCAAGCAGGACCGCC
-60     -50     -40     -30     -20     -10     -1
```

```
    1                        10                              20
    M  E  E  G  Q  Y  S  E  I  E  E  L  P  R  R  R  C  C  R  R
    ATGGAGGAAGGTCAATATTCAGAGATCGAGGAGCTTCCCAGGAGGCGGTGTTGCAGGCGT
    1       10      20      30      40      50      60

30                              40
    G  T  Q  I  V  L  L  G  L  V  T  A  A  L  W  A  G  L  L  T
    GGGACTCAGATCGTGCTGCTGGGGCTGGTGACCGCCGCTCTGTGGGCTGGGCTGCTGACT
            70      80      90      100     110     120

50                              60
    L  L  L  L  W  H  W  D  T  T  Q  S  L  K  Q  L  E  E  R  A
    CTGCTTCTCCTGTGGCACTGGGACACCACACAGAGTCTAAAACAGCTGGAAGAGAGGGCT
            130     140     150     160     170     180

70                              80
    A  R  N  V  S  Q  V  S  K  N  L  E  S  H  H  G  D  Q  M  A
    GCCCGGAACGTCTCTCAAGTTTCCAAGAACTTGGAAAGCCACCACGGTGACCAGATGGCG
            190     200     210     220     230     240

90                              100
    Q  K  S  Q  S  T  Q  I  S  Q  E  L  E  E  L  R  A  E  Q  Q
    CAGAAATCCCAGTCCACGCAGATTTCACAGGAACTGGAGGAACTTCGAGCTGAACAGCAG
            250     260     270     280     290     300

110                             120
    R  L  K  S  Q  E  L  N  E  R  N  E  A  S  D  L  L  E  R  L
    AGATTGAAATCTCAGGAATTGAACGAGAGGAACGAAGCTTCAGATTTGCTGGAAAGACTC
            310     320     330     340     350     360

130                             140
    R  E  E  V  T  K  L  R  M  E  L  Q  V  S  S  G  F  V  C  N
    CGGGAGGAGGTGACAAAGCTAAGGATGGAGTTGCAGGTGTCCAGCGGCTTTGTGTGCAAC
            370     380     390     400     410     420

150                             160
    T  C  P  E  K  W  I  N  F  Q  R  K  C  Y  Y  F  G  K  G  T
    ACGTGCCCTGAAAAGTGGATCAACTTCCAACGGAAGTGCTACTACTTCGGCAAGGGCACC
            430     440     450     460     470     480

170                             180
    K  Q  W  V  H  A  R  Y  A  C  D  D  M  E  G  Q  L  V  S  I
    AAGCAGTGGGTCCACGCCCGGTATGCCTGTGACGACATGGAAGGGCAGCTGGTCAGCATC
            490     500     510     520     530     540
```

```
                         190                             200
   H   S   P   E   E   Q   D   F   L   T   K   H   A   S   H   T   G   S   W   I
  CACAGCCCGGAGGAGCAGGACTTCCTGACCAAGCATGCCAGCCACACCGGCTCCTGGATT
       550         560         570         580         590         600

210                             220
   G   L   R   N   L   D   L   K   G   E   F   I   W   V   D   G   S   H   V   D
  GGCCTTCGGAACTTGGACCTGAAGGGAGAGTTTATCTGGGTGGATGGGAGCCATGTGGAC
       610         620         630         640         650         660

230                             240
   Y   S   N   W   A   P   G   E   P   T   S   R   S   Q   G   E   D   C   V   M
  TACAGCAACTGGGCTCCAGGGGAGCCCACCAGCCGGAGCCAGGGCGAGGACTGCGTGATG
       670         680         690         700         710         720

250                             260
   M   R   G   S   G   R   W   N   D   A   F   C   D   R   K   L   G   A   W   V
  ATGCGGGGCTCCGGTCGCTGGAACGACGCCTTCTGCGACCGTAAGCTGGGCGCCTGGGTG
       730         740         750         760         770         780

270                             280
   C   D   R   L   A   T   C   T   P   P   A   S   E   G   S   A   E   S   M   G
  TGCGACCGGCTGGCCACATGCACGCCGCCAGCCAGCGAAGGTTCCGCGGAGTCCATGGGA
       790         800         810         820         830         840

290                             300
   P   D   S   R   P   D   P   D   G   R   L   P   T   P   S   A   P   L   H   S
  CCTGATTCAAGACCAGATCCTGACGGCCGCCTGCCCACCCCCTCTGCCCCTCTCCACTCT
       850         860         870         880         890         900

TGAGCATGGATACAGCCAGGCCCAGAGCAAGACCCTGAAGACCCCCAACCACGGCCTAAA
       910         920         930         940         950         960

AGCCTCTTTGTGGCTGAAAGGTCCCTGTGACATTTTCTGCCACCCAAACGGAGGCAGCTG
       970         980         990        1000        1010        1020

ACACATCTCCCGCTCCTCTATGGCCCCTGCCTTCCCAGGAGTACACCCCAACAGCACCCT
      1030        1040        1050        1060        1070        1080

CTCCAGATGGGAGTGCCCCCAACAGCACCCTCTCCAGATGAGAGTACACCCCAACAGCAC
      1090        1100        1110        1120        1130        1140

CCTCTCCAGATGCAGCCCCATCTCCTCAGCACCCCAGGACCTGAGTATCCCCAGCTCAGG
      1150        1160        1170        1180        1190        1200

GTGGTGAGTCCTCCTGTCCAGCCTGCATCAATAAAATGGGGCAGTGATGGCC
      1210        1220        1230        1240        1250
```

PREPARATION OF TRANSFORMED HOSTS WHICH EXPRESS BINDING FACTOR RELATED POLYPEPTIDES

This application is a continuation of application Ser. No. 073,788, filed Jul. 15, 1987 now abandoned.

The invention concerns polypeptides related to human immunoglobulin E binding factors (IgE-BFs), mRNAs, DNAs and hybrid vectors coding for said polypeptides, hosts containing said hydrid vectors, and processes for the preparation of said polypeptides, mRNAs, DNAs, hybrid vectors, and hosts. The polypeptides can be used for the prevention and/or the treatment of allergic diseases, and accordingly the invention concerns also pharmaceutical preparations containing them.

BACKGROUND OF THE INVENTION

Allergic diseases are still a major health problem due to their high incidence (20 to 30% of the population) and to the lack of curative treatment. Usually the therapy is restricted to the use of antihistamines or to more or less effective immunization procedures. The classical antiallergic drugs have certain disadvantages, especially since they cause various side effects in the treated patient. The immunization procedure is limited to one or two allergens whereas most of the patients are sensitive to a large number of allergens. In addition, hyposensitization treatment is neither curative nor protective.

The vast majority of allergic diseases are mediated by immunoglobulin E (IgE) antibodies directed against a myriad of airborne allergens, e.g. pollens, animal danders, dust mite, food antigens, pharmacological agents, e.g. penicillins, or hymenoptera venom. The mechanisms regulating the production of IgE have been extensively investigated in laboratory animals [K. Ishizaka, Ann. Rev. Immunol. 2, 159 (1984)]. These studies have clearly indicated the existence of non-antigen specific but IgE isotype specific mechanisms controlling the production of IgE in animal models. The effector molecules of these regulatory mechanisms were named IgE-binding factors (IgE-BFs) owing to their affinity for IgE. IgE-BFs may be divided into IgE-suppressive factors (IgE-SFs) and IgE-potentiating factors (IgE-PFs): These molecules differ only by their carbohydrate content. IgE-SFs are not glycosylated or less glycosylated than the corresponding IgE-PFs. The actual production of IgE in animal models is determined by the ratio between these two kinds of IgE-BFs.

The same cells are capable of secreting either IgE-SFs or IgE-PFs depending on the influence of either glycosylation inhibiting or enhancing factors which are secreted by distinct regulatory T lymphocyte subpopulations.

M. Sarfati et al. [Immunology 53, 197, 207, 783 (1984)] have documented the existence of human B cell lines secreting IgE-BFs endowed with similar biological activities as those described in rodents. Other investigators have described the production of IgE-BFs by human T cells [T. F. Huff and K. Ishizaka, Proc. Natl. Acad. Sci. (U.S.A) 81, 1514 (1984)] and by genetic engineering methods [European Patent Application 155 192]. The relationships between IgE-BFs of T cell origin and those of B cell origin were not known hitherto. As will become evident from the present invention the IgE-BF of B-cell origin has less than statistical homology with the IgE-BF of T-cell origin.

Purified IgE-BFs are important for the diagnosis and therapy of allergic diseases and immune regulation diseases connected therewith. In particular IgE-BFs with IgE-suppressive activity might be useful in the treatment of allergic diseases, whereas IgE-BFs with IgE-potentiating activity might increase resistance to infections, for example resistance to parasitic infections.

Assays for the detection of IgE-BFs from B cells are based on a rosette inhibition test wherein RPMI 8866 cells (a lymphoblastoid B cell line) expressing receptors for IgE ($Fc_\epsilon R$) are rosetted with IgE-coated bovine erythrocytes. If the latter are first preincubated with IgE-BFs, they are no longer able to bind to RPMI 8866 cells and the proportion of cells forming rosettes is reduced accordingly. This assay is not quantitative, it is technically delicate due to the variability in the coupling of IgE to bovine erythrocytes and it is cumbersome, because rosettes must be examined under the microscope, cell lines must be permanently available, IgE-coated erythrocytes must be prepared regularly, etc., so that only a small number of tests (20-40) can be performed reasonably by one person in one day. In a more convenient, quantitative and easy to perform assay monoclonal antibodies to lymphocyte $Fc_\epsilon R$ which are crossreacting with IgE-BFs are utilised. Such monoclonal antibodies have been prepared by G. Delespesse et al., EP 86810244.3, and the hybridoma cell lines producing them are deposited at the Collection Nationale de Cultures de Microorganismes, Institute Pasteur, Paris and are available under accession No. I-425 (clone 208.25 A. 4,3/135), I-420 (clone 208.25 D. 2,1/176), I-451 (clone 207.25 A. 4,4/30), I-452 (clone 207.25 A.4,4/45), and I-486 (clone 208.25 D. 2/94). The corresponding monoclonal antibodies are named Mab-135, Mab-176, Mab-30, Mab-45 and Mab-94, respectively. They allow also an efficient purification of IgE-BFs by affinity chromatography.

Despite the use of above monoclonal antibodies it was hitherto impossible to determine the amino acid sequence of a single IgE-BF isolated from a natural human B-cell line. For therapeutic purposes it would be highly desirable to have a clean, single polypeptide with a defined amino acid sequence having the desired IgE-binding property, and which can be easily prepared in large amounts.

The fast progress in recombinant DNA methods in recent years provides the general methods for achieving this goal. In cases, where the sturcture of the polypeptide is unknown, the sucess of the recombinant DNA technique depends on identification of a mRNA or a DNA coding for the desired polypeptide from a natural source.

After identification of a mRNA by means of a suitable assay, a complementary DNA can be prepared. The cDNA can be incorporated into a suitable vector, whereupon transformation of a suitable host with the obtained hybrid vector, selection and culturing of the transformed hosts allows production and finally isolation of the polypeptide. Isolation of the cDNA coding for the desired polypeptide and sequencing allows determination of the amino acid sequence of the polypeptide. The cDNA or parts thereof can be used to screen the mRNA or the DNA genome of the natural source for further nucleotide sequence coding for the desired polypeptides.

Accordingly, in the present invention, as the structures of the IgE-BFs were unknown, the first objective was to identify a mRNA of human B-cells coding for the desired polypeptide by transforming eggs of Xenopus laevis with fractioned mRNA of said B-cells and determining the clones containing the desired mRNA by an assay utilizing the above monoclonal antibodies. Further objectives were the preparation of cDNAs, and hybrid vectors, the transformation of suitable hosts and finally culturing said hosts and isolating the desired polypeptides. The latter are not necessarily identical with the naturally occurring polypeptides because post-translational modifications can take place after expression of the polypeptide.

OBJECTS OF THE INVENTION

The objects of the invention are polypeptides related to IgE-BFs of human B-cells, hybrid vectors comprising as an insert a DNA sequence coding for said polypeptides, transformed hosts containing said hybrid vectors, RNA and DNA molecules coding for said polypeptides and pharmaceutical preparations containing effective amounts of said polypeptides.

Further objects are methods for the production of said polypeptides, hybrid vectors, transformed hosts, RNA and DNA molecules, pharmaceutical preparations and the use of said polypeptides.

Another object of the invention is to provide a method for the prevention and/or treatment of allergy by administering an effective amount of a present polypeptide related to IgE-BFs.

These objects have been achieved by the preparation of a DNA coding for the polypeptide of the formula I and fragments thereof.

DESCRIPTION OF THE INVENTION

The Polypeptides of the Invention

The invention concerns a polypeptide having the amino acid sequence of the formula (I) given in FIG. 9, a fragment, mutant or derivative thereof.

The polypeptides of the formula I, fragments, mutants and derivatives thereof are grouped together herein under the uniting expression "polypeptides of the invention". They are related to the IgE receptors on human B-cells and, if without the membrane anchoring sequence, to the IgE-BFs of Sarfati et al., mentioned above.

Fragments of the polypeptides of the invention are parts of the complete polypeptide of the formula (I) having at least 10 and up to 320 successive amino acids in a sequence corresponding to the formula (I). Such fragments are for example polypeptides of the formula (I), wherein the first amino acid, or up to about 133 amino acids starting from the N-terminal are deleted. This deleted N-terminal is the membrane-anchoring sequence binding the polypeptide to the cytoplasmic membrane of the B-cells. Other fragments are polypeptides of the Formula (I), wherein amino acids between the N- and the C-terminal, for example amino acids of about 110 to 130, or amino acids at the C-terminal, for example amino acids of about 250 to 321, are deleted.

The invention in particular relates to a fragment of the polypeptide of the formula (I), characterized in that the amino acid sequence comprising amino acids 106 to 127 is deleted; or that it is selected from the group consisting of polypeptides starting with anyone of amino acids 120, 121, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159 or 160 and ending with any one of the amino acids between 282 and 321, preferably 321.

A preferred fragment of the polypeptide of the formula (I) is characterized in that it consists of the amino acid sequence from amino acid 119 to amino acid 321.

Another preferred fragment of the polypeptide of the formula (I) is characterized in that it consists of the amino acid sequence from amino acid 134 to amino acid 321.

Another preferred fragment of the polypeptide of the formula (I) is characterized in that it consists of the amino acid sequence from amino acids 148 or 150 to amino acid 321. These two fragments can be found in supernatants of RPMI 8866 cells, and thus correspond to naturally occurring IgE-BF.

The fragments may have a methionine attached to the N-terminal, especially when obtained from expression in *E. coli*.

Mutants of the polypeptides of the invention are characterized in the exchange of one (point mutant) or more, about up to 10, of its amino acids against one or more of another amino acid. They are the consequence of the corresponding mutations at the DNA level leading to different codons.

Derivatives of the polypeptide of the invention, are such where functional groups, such as amino, hydroxyl, mercapto or carboxyl groups, are derivatized, e.g. glycosylated, acylated, amindated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulfuric acid, which usually takes place at the N-terminal amino group, or at hydroxy groups, especially of tyrosine or serine, respectively. Esters are those of naturally occurring alcohols, e.g. methanol or ethanol.

Further derivatives are salts, especially pharmaceutically acceptable salts, for example metal salts, such as alkali metal and alkaline earth metal salts, e.g. sodium, potassium, magnesium, calcium or zink salts, or ammonium salts formed with ammonia or a suitable organic amine, such as a lower alkylamine, e.g. triethylamine, hydroxy-lower alkylamine, e.g. 2-hydroxyethylamine, and the like.

Polypeptides of the formula (I) have IgE-binding activity as can be demonstrated by the rosette inhibition assay and the binding to monoclonal antibodies, e.g. to Mab-135 and Mab-176, which are specific for IgE-BFs. Of the fragments, mutants and derivatives those are preferred having IgE-binding activity.

The polypeptides of the invention are prepared by recombinant DNA techniques comprising the identification of a mRNA coding for such a polypeptide, preparation of a DNA or cDNA, construction of a cDNA hybrid vector, transformation of a host cell which allow the expression of said vector and isolation of said polypeptides.

Accordingly, the invention concerns further a method for the production of a polypeptide of the formula (I), a fragment, a mutant or a derivative thereof, characterized in that a) a transformed host containing a hybrid vector comprising a DNA sequence coding for a polypeptide of the formula (I), a fragment or mutant thereof, is cultured, or b) the mRNA coding for a polypeptide of the formula (I), a fragment or mutant thereof is translated in an appropriate translation system, and, when required, a polypeptide of the formula (I), a fragment or mutant thereof is transformed into a derivative thereof.

a) Transformed hosts are selected from prokaryotic or eukaryotic cells, e.g. bacteria, fungi, e.g. yeasts, or higher cells, including human cell lines. Preferred are available *E. coli* strains, e.g. HB 101, BZ 234, B1472, or available S. cerevisiae strains, e.g. RH971, which are transformed with a hybrid vector coding for a polypeptide of the invention and containing appropriate promoter, enhancer, marker and signal sequences, and the like.

The transformed host cells are cultured by methods known in the art, usually in a liquid medium containing assimilable sources of carbon, nitrogen and inorganic salts and, if necessary appropriate growth factors.

For the growth of transformed pro- and eukaryotic microorganisms, various sources of carbon can be used. Examples of preferred sources of carbon are assimilable carbonhydrates, such as glucose, maltose, mannitol or lactose, or an acetate, which can be used either by itself or in suitable mixtures. Examples of suitable sources of nitrogen are amino acids, proteins, such as tryptone, peptone or meat extracts, yeast extracts, malt extracts and also ammonium salts, for example ammonium chloride or nitrate, which can be used either by themselves or in suitable mixtures.

The medium furthermore contains trace elements, for example $K^+$, $Ca^{2+}$, $Mg^{2+}$, $Fe^{2+}$, $Mn^{2+}$, $Zn^{2+}$, $Cu^{2+}$, $NO_3^-$, $SO_4^{2-}$, $HPO_3^{2-}$, $H_2PO_4^-$, $Cl^-$, $BO_3^{3-}$ and $MoO_4^{2-}$ ions. Also substances are preferably added which exert a selection pressure and prevent the growth of cells which have lost the expression vector. Thus, for example, ampicillin is added to the medium if the hybrid expression vector contains an $amp^R$ gene. The addition of antibiotic substances also has the effect that contaminating antibiotic-sensitive microorganisms cannot survive. If a yeast strain which is auxothropic in, for example, an essential amino acid, is used as the host microorganims, the plasmid preferably contains a gene coding for an enzyme which complements the host defect. The cultivation of the yeast strain is performed in a minimal medium deficient in said amino acid.

Vertebrate cells are grown under tissue culture conditions using commercially available media (e.g. Gibco, Flow Laboratories) supplemented in most cases with serum of a mammal. The cells are grown in large scale either attached to a solid support, such as roller bottles, microcarriers and porous glass fibers, or they are grown as free-floating cells in appropriate vessels.

The cultivation is effected by processes which are known in the art. The culture conditions, such as temperature, pH value of the medium and fermentation time, are chosen so that a maximum titre of the polypeptide of the invention is obtained. Thus, an *E. coli* or yeast strain is preferably cultured under aerobic conditions by submerged culture with shaking or stirring at a temperature of about 20 to 40° C., preferably about 30° C., and a pH value of 4 to 8, preferably at about pH 7, for about 4 to 30 hours, preferably until maximum yields of the polypeptide of the invention are reached.

b) The mRNA coding for a polypeptide of the invention can be translated and expressed in an appropriate translation system, such as the oocytes of Xenopus laevis. mRNA coding for the polypeptides of the invention is microinjected into oocytes of the female frog Xenopus laevis. The transformed oocytes are incubated in Barth solution, supplemented with FCS at about 20° C. for about 45 hours. After removal of the incubation medium the oocytes are homogenized in oocyte lysis buffer and centrifuged. The supernatant contains the polypeptides of the invention as can be shown by a RIA assay using monoclonal antibodies. This method of producing the polypeptides of the invention is mainly useful for indentification purposes.

When the level of the polypeptide of the invention has reached a maximum, the culture is interrupted and the polypeptide can be isolated. If the polypeptide is fused with a suitable signal peptide sequence, it is secreted by the cell directly into the supernatant. Otherwise, the cells have to be destroyed, for example by treatment with a detergent, such as SDS or tritone, or lysed with lysozyme or a similarly acting enzyme. If yeast is used as host microorganism, the cell wall may be removed by enzymatic digestion with a glucosidase. Alternatively or additionally, mechanical forces, such as shearing forces (for example X-press, French-press, Dyno mill) or shaking with glass beads or aluminum oxide, or alternating freezing, for example in liquid nitrogen, and thawing, as well as ultra-sound can be used to break the cells. The proteins of the cell supernatant or the mixture obtained on breaking the cells, including the polypeptides of the invention, are enriched by methods well known in the art, in particular by polyethyleneimine treatment, centrifugation and precipitation with salts, e.g. ammonium sulphate or zink salts. Further purification steps are, for example, ultracentrifugation, diafiltration, gel electrophoresis, chromatographic processes, such as ion exchange chromatography, size exclusion chromatography, high pressure liquid chromatography (HPLC), reverse phase HPLC, fast pressure liquid chromatography (FPLC) and the like, separation of the constituents of the mixture according to molecular size by means of a suitable gel filtration column, dialysis, affinity chromatography, for example affinity chromatography using antibodies, especially monoclonal antibodies, in particular Mab-135 and Mab-179, and other processes known in the art.

In a preferred embodiment the polypeptides of the invention are isolated from the cell supernatants by filtering the supernatant through a monoclonal antibody affigel, e.g. Mab-45-affigel, eluting the bound IgE-BF polypeptide, e.g. with a 0.1 M glycine-HCl buffer of pH 2.6, loading the fractions containing the desired polypeptide onto an anion exchanger column, e.g. SynChropak AX 300, washing the column, e.g. with a Tris-HCl buffer, pH 7.4, eluting the protein, e.g. with a sodium chloride solution, such as 1 M NaCl, dialyzing and lyophilizing the fractions containing the desired polypeptide, subjecting the dialyzed fractions to a reversed phase chromatography, e.g. on a SynChropak RP-4 column, and eluting the desired polypeptide, e.g. with acetonitrile/0.1% TFA gradient.

This method is especially suitable for the purification of natural IgE-BF from RPMI 8866 cell supernatants. The natural IgE-BF purified by this method was pure enough for an amino acid sequencing procedure, which revealed that it consists of two proteins, the N-terminal amino acid sequences being the following:

```
  148 149         155         160    163
    L X M E L Q V X S G F V X N T X P
``` and

-continued $$\underset{150}{M} \underset{151}{X} L Q V S S G F \underset{160}{V} X N T \underset{163}{X} P E K.$$

The numbering corresponds to the numbering of formula (I). The amino acids designated with an X were not determined, however by comparison with the DNA sequences of the formula II or III the following designation can be made: $X_{149}=R$, $X_{151}=E$, $X_{155}=S$, $X_{160}=C$, $X_{163}=C$. The analysis allows the conclusion that natural IgE-BF consists of at least two polypeptides with the amino acid sequences extending from $L_{148}$ to $S_{321}$ and $M_{150}$ to $S_{321}$ (formula I), and which occur in a proportion of about 40 to 60.

Finally, the IgE-binding activity of the isolated protein can be determined by methods well known in the art, e.g. by the rosette inhibition assays, the blocking of IgE-binding to anti-IgE antibodies, affinity chromatography experiments, and experiments measuring the suppression of the ongoing in vitro IgE synthesis by lymphocytes from allergic individuals.

Polypeptides of the invention having the correct sequence, however the wrong threedimensional folding, are useful as intermediates in renaturation experiments.

The invention concerns also a polypeptide of the formula (I), a fragment, mutant or derivative thereof, whenever obtained according to a process of the invention.

Preparation of Transformed Hosts

The invention further concerns a multistep method for the preparation of a transformed host capable of expressing a polypeptide of the invention, characterized in 1. preparing a DNA coding for a polypeptide of the formula (I), a fragment, mutant or derivative thereof,
2. incorporating the obtained DNA into an appropriate vector,
3. transforming an appropriate host with the obtained hybrid vector,
4. selecting the transformed hosts from untransformed hosts, and, optionally, isolating the hybrid vector from the transformed host, modifying the coding or non-coding region of the hybrid vector and performing steps 3 and 4 again.

The steps involved in the preparation of the hosts are discussed in more detail hereinbelow. The invention concerns also the single steps.

1. Preparation of a DNA Coding for a Polypeptide of the Invention

The invention concerns a DNA coding for a polypeptide of the formula I, a fragment, mutant or derivative thereof, and methods for the preparation.

The DNA coding for a polypeptide of the invention can be obtained a) by reverse transcription of isolated mRNA into cDNA, b) by isolation from genomic DNA or c) by chemical synthesis.

In the present invention, as long as the DNA structure was unknown, the DNA had to be obtained from genomic DNA or a cDNA library via the mRNA. A cDNA library comprises the genetic information which is complementary to the mRNA isolated from cells.

a) Reverse Transcription of Isolated mRNA into cDNA

To obtain a cDNA library the mRNA is isolated from cells expressing IgE-binding activity, especially human B-cells and cell lines derived thereof. This mRNA is converted into double stranded cDNA. A preferable human B-cell line is RPMI 8866. Other useful B-cell lines can be prepared by immortalizing natural B-cells with Epstein-Barr-virus. Standard methods well known in the art are applied in the preparation of mRNA. The cell membrane is broken and the cell content released from which the mRNA is isolated. The cell membrane is preferably broken by physical methods or lysis with detergents such as SDS, guanidinium thiocyanate, definite salt conditions or homogenisation, preferably by mixing. The mRNA is isolated by the standard methods of phenol extraction, ethanol precipitation, centrifugation and chromatography, preferably a combination of several methods. Centrifugation is preferably done over gradients, per example over a CsCl gradient. For chromatography preferably columns are used, specially oligo-dT columns.

The total mRNA can be converted directly into ds-cDNA following the methods of the art. Preferably the mRNA coding for a polypeptide of the invention is further enriched using several techniques, such as electrophoresis, chromatography and centrifugation, preferably sucrose gradient centrifugation.

Fractions containing mRNA coding for a polypeptide of the invention can be detected by several methods, such as in vivo or in vitro translation followed by detection of IgE-binding factor activity or, now, as the nucleotide sequence is known, by hybridization with an oligonucleotide probe.

In vivo translation systems can be prokaryotic or eukaryotic systems. A preferred in vivo translation system is the Xenopus laevis oocyte system as described by Maniatis et al. (1). In vitro systems are per example wheat germ and rabbit reticulocyte lysates, both commercially available.

Detection systems to screen for IgE binding factor property use preferably monoclonal antibodies against the polypeptide of the formula (I), especially Mab-135 or Mab-176. Another possible system uses immunoglobulins of the IgE type in conventional immunoassays.

From any pool of mRNA derived from unfractionated or fractionated mRNA, ds-cDNA can be obtained by the well known methods of the art. Preferred general methods are described by Maniatis et al. (1), Okayama and Berg (2) and Heidecker et al. (3). In general the mRNA is converted first to ss-cDNA using the enzyme reverse transcriptase and then to double stranded cDNA using the enzymes reverse transcriptase or DNA polymerase I (Klenow fragment). In this invention the procedure is preferably done according to the method described by Maniatis et al. (1). Two methods are alternatively used for priming the synthesis of the ds-cDNA. The first method uses the natural loop formation of the ss-cDNA. The second method is done by tailing of the ss-cDNA with a homopolymeric tail such as poly-dC or poly-dT.

The mRNA fraction of which the corresponding polypeptide shows the highest activity in the detection system is transcribed into the complementary cDNA by methods well known in the art. The mRNA and oliog-dT as a primer are mixed. Then, dNTPs are added as starting material and the synthesis of the cDNA-mRNA hybrid molecule is realized by the enzyme reverse transcriptase. The RNA molecules are degraded by addition of NaOH. DNA polymerase is admixed, preferably the Klenow fragment of the DNA polymerase I, and the mixture is incubated at a suitable temperature, preferably 12°–15° C. The mixture is incubated with nuclease S1 and the ds-cDNA corresponding to the mRNA coding for a polypeptide of the invention is obtained.

For amplification and structure elucidation the obtained ds-cDNA is spliced into a suitable vector, e.g. the plasmid pUC-KO, and the obtained hybrid vector is multiplied by use of a suitable host, e.g. *E. coli* HB101, as in more detail is described hereinbefore Reisolation of the hybrid vectors, and recovering the inserted cDNA therefrom allows a structure determination of the DNA coding for a polypeptide of the invention. The obtained hybrid vectors pCL-2 and pCL-1 contain inserts of the formulae (II) and (III) given in FIG. 10 and FIG. 11, respectively. The cDNA of formula (II), FIG. 10, comprised in pCL-2 contains the entire coding region for the peptide of formula (I), FIG. 9, and the non-coding flanking regions which are also part of the non-coding region of the isolated mRNA. In the cDNA of formula (III), FIG. 11, comprised in pCL-1 the nucleotides coding for amino acids 106 to 127 of the polypeptide of formula (I), FIG. 9, i.e. nucleotides 316 to 378 of formula (II), FIG. 10, are deleted, and the coding region and part of the two flanking sequences are identical to the DNA-Sequence of the formula (III), FIG. 11.

b) Another suitable method to obtain the DNA coding for a polypeptide of the invention consists in the isolation of said DNA from the genomic DNA of tissue or a cell culture. The cells are lysed, preferably with SDS and proteinase K, and the DNA is deproteinized by repeated extraction with phenol. The RNA is preferably digested with RNAse. The obtained raw DNA is partially digested with suitable restriction enzymes, e.g. HaeIII and AluI, and fragments of 15-20 Kb are isolated, and multiplied in a suitable phage or cosmid, e.g. in Charon 4A or EMBL-3 phage, and assayed for the desired sequences, e.g. with a radioactively labeled DNA probe or otherwise as described hereinbefore.

c) A third method for preparation of the DNA coding for a polypeptide of the invention is the chemical synthesis. Chemical syntheses of DNA have been presented in summary form by S. A. Narang (4). The known synthesis techniques allow the preparation of polynucleotides up to 40 or 60 bases in good yield, high purity and in relatively short time. Suitably protected nucleotides are linked by the phosphodiester method of K. L. Agarwal et al. (5), the phosphotriester method of C. B. Reesem (6) or the phosphite triester method of R. L. Letsinger et al. (6a). Simplification of the synthesis of the oligonucleotides and polynucleotides is possible by the solid phase method, in which the nucleotide chains are bound to a suitable polymer. Advantageously a DNA synthetizing machine is used.

The actual double stranded DNA can be built up enzymatically from chemically prepared short but overlapping segments. For example, according to Khorana et al. (7), overlapping polynucleotide sequences from both DNA strands are used, which are held together in the correct arrangement by base pairing and are then chemically linked by the enzyme DNA ligase. Another possibility comprises incubating in each case one polynucleotide sequence from the two DNA strands with a short overlapping segment in the presence of the four required deoxynucleoside triphosphates with a DNA-polymerase, for example DNA-polymerase I, the Klenow fragment of polymerase I or T4 DNA polymerase, or with reverse transcriptase. The two polynucleotide sequences are thereby held together in the correct arrangement by base-pairing and are supplemented with the required nucleotides by the enzyme to give a complete double-strand DNA (S. A. Narang et al. (8)).

d) Preparation of DNAs Coding for a Fragment of the Polypeptide of the Formula (I)

DNAs coding for a fragment of the polypeptide of the formula (I) are obtained in that the DNA of the formula (II) or (III), or a vector containing it, is digested with a suitable restriction enzyme and/or a suitable exonuclease, and, when required, the DNA fragment obtained is supplemented with a DNA fragment synthetized by chemical methods, or the desired fragment is totally synthetized by chemical methods.

Suitable restriction enzymes and their restriction sites are shown in formula (II). For the preparation of the DNA fragments coding for the polypeptide sequence $D_{119}$ to $S_{321}$ of the formula (I), Bgl II and Rsa I are suitable. The DNA fragment coding for the polypeptide sequence $A_{134}$ to $S_{321}$ can be obtained by restriction with HindIII and RsaI (see Formula II, FIG. 4). The preparation of the DNA fragments can also be achieved stepwise, in that first a larger DNA fragment is prepared, e.g. by restriction with HincII and RsaI, which is subcloned in a suitable vector, which is consecutively cut with BglII and BamHI, or HindIII, respectively (see FIGS. 3 and 4).

The chemical synthesis, either total or partial, in combination with the use of restriction enzymes and/or exonucleases, allows the preparation of any desired DNA fragment comprised by formula (II).

The invention concerns further DNA fragments of the DNA of the formula (II). The fragments are either coding for a polypeptide having IgE-binding activity or can be used as probes for identifying such DNA from natural or synthetic sources. Preferred DNA fragments are those coding for the preferred polypeptide fragments comprised by formula (I). DNA probes have at least 7, preferably about 15 nucleotides in sequence.

2. Preparation of a Hybrid Vector

A hybrid vector of the invention is prepared in that a DNA coding for a polypeptide of the formula (I), a fragment, mutant or derivative thereof is spliced into a suitable vector.

Suitable vectors are carriers for integrated passenger DNA, which can be used to transform a host microorganism, including human cells, and which can replicate within the host. Suitable as vectors are plasmids, phages or cosmids. Suitable vectors carry the insert DNA at a defined position.

In general, such vectors contain a replicon and a control sequence, i.e. a promoter, which are derived from species compatible with the host cell wherein they are used. The vector ordinarily carries a replicon site, as well as sequences (marker genes) which are capable of providing phenotype selection in transformed cells. Suitable marker genes award, per example, resistance to antibiotics or heavy metals to the host or they complement a genetic defect of the host. Further useful sequences in such vectors are enhancer and activator sequences.

The starting vectors are suitable for use in host cells over a wide range of prokaryotic and eukaryotic organisms. The vector is selected depending on the host cells envisaged for transformation.

Preferred starting vectors are plasmid DNA's and bacteriophage DNA's available in the art. In particular the plasmid pBR322 and derivatives thereof are useful. Such derivatives are, per example, the plasmids pUC-8, pUC-9, pMB-9, pGEM TM-1 and pGEM TM-2. Of the bacteriophage vectors the DNAs of the lambda phages are preferred, per example, the DNA of the lambda phage gt-11. Further suitable phage vectors are the Charon 4A and EMBL-3 phage. The lambda cloning systems are described by Maniatis et al. (1).

A vector carrying a passenger DNA such as of the formula (II) or (III), is designated as hybrid vector.

The obtained DNA is spliced into the starting vector by conventional methods.

A starting plasmid, for example, is first linearized by a suitable restriction enzyme, e.g. the plasmid pUC-KO by PstI, then d/G-tailed in the presence of dGTP and terminal deoxynucleotidyl transferase. The double stranded cDNA insert is dC-tailed in the presence of dCTP and terminal deoxynucleotidyl transferase. Combining both, cDNA and vector, results in the hybrid vector. Bacteriophages, such as lambda, are preferred for constructing genomic libraries. The lambda cloning systems are described by Maniatis et al. (1). The suitable vector DNA is digested to completion with the appropriate restriction enzyme, and the left and the right arms are separated from the central fragments by velocity gradient centrifugation or gel electrophoresis. Another method is to digest parts of the stuffer fragments with restriction enzymes which lack recognition sites in the left and the right arm. The isolated genomic DNA is partially digested to fragments of 15-20 kb in length. Afterwards the arms are ligated with the fragments of foreign DNA having termini compatible with those of the arms.

The appropriate DNA insert is recloned from the original vector used for the original cloning, into a suitable expression vector. To this end, appropriate restriction enzymes (FIGS. 3 and 4) are used, eventually in combination with exonucleases, in particular Bal31, to produce the desired DNA fragments. These fragments are integrated into an appropriate expression vector by using the cohesive ends directly or by the addition of appropriate chemically synthesized oligonucleotide bridges. For the modification of the ends, per example, HindIII and BglII can be used. The method is not limited to these special restriction enzymes. Any desired link can be made between the expression vector and the DNA insert using suitable restriction enzymes in combination with chemically synthesized oligonucleotides.

The invention also relates to a hybrid vector comprising a DNA coding for a polypeptide of the formula (I), a fragment, a mutant or a derivative thereof, operatively linked to an expression control sequence.

For the expression a suitable hybrid expression vector is used. The term hybrid expression vector includes special vectors which are capable of expressing DNA sequences contained therein, where such sequences are operably linked to other sequences capable of effecting their expression, i.e., operator, enhancer and promoter sequences. In sum, expression vectors are characterized in a functional definition: any DNA sequence which is capable of effecting expression of the specified DNA sequence disposed therein. The invention is intended to include all forms of hybrid expression vectors which can be made from an expression vector known in the art and functional equivalents containing the DNA inserts coding for a polypeptide of the invention.

Several expression control sequences can be used for regulation of the gene expression. The microbial expression vectors normally contain promoters which are used by the microbial host for expression of its own proteins. Those promoters most commonly used in recombinant DNA constructions include the $\beta$-lactamase and lactose promoter systems (Chang et al. (9); Goeddel et al. (10), the tryptophan (trp) promoter system (Goeddel et al. (11)), or a bacteriophage promoter system such as the $P_L$ promoter from lambda.

While these are the most commonly used, other microbial promoters have been discovered and utilized, and details concerning their nucleotide sequences have been published, enabling a skilled worker to ligate them functionally with plasmid vectors (Siebenlist et al. (12)). In principle, all vectors which replicate and express the polypeptides of the invention in the chosen host are suitable. Examples of vectors which are suitable for the expression of said polypeptide are the plasmids pKK223-3, pDR720 and pPL-lambda or the vectors of the bacteriophage lambda such as $\lambda$-gtll, all commercially available (Pharmacia, Sweden; Promega Biofec, USA). The preferred vectors of the present invention are the expression and secretion vectors of the type pIN-ompA (Gharayeb et al. (13)) and vectors containing the PL promoter.

Vectors which are suitable for replication and expression in yeast contain one or more, e.g. two, yeast replicon starts and one or more selective genetic markers for yeast. Hybrid vectors which contain a yeast replicon start, for example a chromosomal autonomously replicating segment (ars 1) or the $2\mu$ ori, are retained extrachromosomally within the yeast cell after the transformation and are replicated autonomously. Suitable marker genes for yeast are, in particular, those which impart antibiotic resistance to the host or, in the case of auxotrophic yeast mutants, genes which complement host lesions. Corresponding genes impart, for example, resistance towards the antibiotic cycloheximide or provide for protrophy in an auxotrophic yeast mutant, for example the URA3, LEU2, HIS3 or, in particular the TRP1 gene. Yeast hybrid vectors furthermore preferably contain a replicon start and a marker gene for a bacterial host, in particular E. coli, so that the construction and cloning of the hybrid vectors and their intermediates can take place also in a bacterial host (shuttle vectors). Expression control sequences which are suitable for expression in yeast are, for example, those of highly expressed yeast genes. Thus the promotors of the TRP1 gene, the ADHI or ADHII gene, phosphatase (PHO3 or PHO5) gene, isocytochrome gene or a promotor involved with the glycolytic pathway, such as the promoter of the enolase, glyceraldehyd-3-phosphate dehydrogenase (GAPDH) or 3-phosphoglycerat kinase (PGK), can be used.

Preferred vectors contain promoters which can be turned on or off by variation of the growth conditions. For example the PHO5 promoter can be repressed or derepressed solely by increasing or decreasing the concentration of inorganic phosphate in the medium.

Expression vectors for such cells ordinarily include a versatile and strong enhancer/promoter unit located in front of the gene to be expressed. If cDNA is to be expressed, RNA splice sites, polyadenylation sites and eventually a transcriptional terminator sequence are added to the gene. For use in mammalian cells the control functions on the expression vectors are often provided by viral material. For example, commonly used enhancer-promoters units are derived from Simian virus 40 (SV40), Rous sarcoma virus, Adenovirus 2, or mouse and human cytomegalovirus. In particular, the enhancer promoter unit of the mouse cytomegalovirus immediate early gene and the SV40 enhancer combined with the human α-globin promoter are suitable. In addition, inducible promoters, such as the ones derived from the heat shock or metallothionine genes are useful. Further it is also possible to utilize promoter or control sequences which are normally associated with the desired gene sequence. An origin of replication may be provided either by construction of the vector to include an exogenous origin, such as derived from SV40 or other viral source (e.g. Polyoma, Adeno, VSV, SPV, etc.), or provided by the host cell chromosomal replication mechanism. If the vector is integrated into the host cell chromosome, the latter method is often more sufficient.

The reisolation of the vector DNA containing the cloned DNA insert from a host is achieved according to the art, in particular by lysis of the host cell and purification of the DNA by centrifugation, in particular CsCl density centrifugation and phenol/chloroform extraction.

The invention relates also to hybrid vectors comprising as an insert a DNA sequence coding for a polypeptide of the formula (I) or a fragment, a mutant or a derivative thereof.

In particular, the invention concerns a hybrid vector comprising as an insert a DNA sequence coding for a fragment of the polypeptide of the formula (I), characterized in that the insert is coding for a polypeptide of the formula (I), wherein the amino acid sequence comprising amino acids 106 to 127 are deleted; or a fragment of the polypeptide of the formula (I), which is selected from the group consisting of polypeptides starting with anyone of amino acids 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159 or 160 and ending with anyone of the amino acids between 282 and 321; or a fragment of the polypeptide of the formula (I), which consists of the amino acid sequence from amino acid 119 to amino acid 321; or a fragment of the polypeptide of the formula (I), which consists of the amino acid sequence from amino acid 134 to amino acid 321; or a fragment of the polypeptide of the formula (I) which consists of the amino acid sequence from amino acid 148 to amino acid 321; or a fragment of the polypeptide of the formula (I) which consists of the amino acid sequence from amino acid 150 to amino acid 321.

In particular the invention concerns a hybrid vector comprising a DNA sequence of the formula (II) or (III), or a fragment or mutant thereof.

Specific hybrid vectors are pCL2, pCL1, pFK-1, pFK-2, pPL-BF, pJDB207R/PHO5-BF, pCAL5-R/ND, pCAL8-BF/ND and pPL.PTIS-BF (FIGS. 1 to 8).

A further hybrid vector according to the invention comprises a DNA sequence of at least 15 nucleic acids which is 100% homologous to a part of the insert of the formula (II).

3. Transformation of a Host

Next to a powerful expression vector a compatible host cell is used for the expression of the desired polypeptide of the invention. In general prokaryotes are preferred for cloning of DNA sequences and assembling the vectors. The assembled vectors are then transferred into suitable host cells, whereby prokaryotic as well as eukaryotic cells may be used. Microbial species which may be used include E. coli, Bacillus subtilis, Bacillus staerothermophilus and other enterobacteriaceae, such as Salmonella typhimurium or Serratia marcesans, and various pseudomonas species. In particular, E. coli strains such as E. coli B, HB101, BZ234, X1776, W3110, JA221 and K12 are useful. These examples are, of course, intended to be illustrative rather than limiting.

In addition to prokaryotes, eukaryotic microbes, such as yeast may also be used. Saccharomyces cerevisiae, or common baker's yeast is the most commonly used among eukaryotic microorganisms, although a number of other species are commonly available. For expression in Saccharomyces, for example the plasmid YRp7 (Stinchomb et al. (14); Kingsman et al. (14a), Tschemper et al. (15)) can be used.

In addition to microorganisms, cultures of cells derived from multicellular organisms may also be used as hosts. In principle, any such cell culture is workable, whether from vertebrates or invertebrates; however, vertebrate cell cultures are of greater interest. Example for such useful host cell lines are Vero and Hela cells, Chinese hamster ovary (COH) cell lines, Bowes melanoma cell lines, RPMI 8866, and Cos-7 cell lines.

The transformation of the obtained hybrid vector DNA into a recipient is achieved by methods well known in the art, e.g. as described by Maniatis et al. (1). Bacteria are transformed with the hybrid vector DNA e.g. by the CaCl transformation method.

Another suitable transformation method for E. coli host bacteria, in connection with the DNA of lambda phages as a vector, is in vitro packaging of the hybrid vector DNA and infection of said bacteria. In vitro packaging is mainly achieved by using available packaging kits (Pharmacia, Sweden; Boehringer, Mannheim). The infection is done by the $MgCl_2$ method as described by Maniatis (1), page 275.

The transformation of yeast comprises, for example, the steps of enzymatic removal of the yeast cell wall by means of glucosidases, treatment of the obtained spheroplasts with the vector in the presence of polyethylene glycol and $Ca^{2+}$-ions and regeneration of the cell wall by embedding the spheroplasts into agar. Preferably, the regeneration agar is prepared in a way to allow regeneration and selection of the transformed cells at the same time.

The transformation of vertebrate cells grown in tissue cultures is achieved by using one of several methods well known in the art. Direct microinjection of the DNA into the cell nucleus, fusion of E. coli protoplasts with the future host cell or the addition of co-precipitates between DNA and calcium phosphate can be used. The subsequent selection of transformed cells can be done using a selection marker which is either covalently integrated into the expression vector or added as a separate entity. Selection markers include genes which confer resistance to antibodies such as G418 and hygromycin, or genes which complement a genetic lesion of the host cell such as the absence of thymidin kinase or hypoxanthine phosphoribosyl transferase.

4. Selection of Transformed Hosts

Transformed hosts carrying the properties of the selection units integrated into the vectors are selected from untransformed hosts especially by growing up the bacteria under appropriate selection conditions, whereby only the transformed hosts survive. Another method for selection, in connection with bacteriophages is the plaque formation on plated *E. coli* host bacteria.

The screening for hosts carrying a hybrid vector comprising as an insert a DNA sequence coding for a polypeptide of the invention can be achieved by using radioactively marked oligonucleotide probes coding for a fragment of such polypeptide or by screening for the polypeptide product of said DNA insert. The hybridization is done especially with mRNA or any oligonucleotide probe containing about 12 or more consecutive nucleotides coding for a fragment of a polypeptide of the invention.

In particular, the selection of *E. coli* hosts transformed by hybrid vectors, carrying an insert coding for a polypeptide of the invention may be performed by means of hybridization of a oligonucleotide probe to replica filters derived from a cDNA library which is spread on agarose plates. The oligonucleotide can be labelled at the 5'-end with $^{32}$P-$\alpha$ATP using the enzyme T$_4$-kinase or internally by a primed synthesis with Klenow polymerase using any fragment of the cDNA coding for a polypeptide of the invention cloned into the phage M13.

The protein product for screening purposes is obtained by in vitro or in vivo translation in particular using the Xenopus laevis oocyte system, as described by Maniatis et al. (1). The translated protein product is detected by using monoclonal antibodies, such as Mab-45, Mab-176 and Mab-135, or by using a functional test system such as binding of the IgE to the polypeptide as done in the rosette inhibition test by Sarfati et al. (17).

Recombinant phages carrying a DNA sequence coding for a polypeptide of the invention are identified by hybridization whereby a radioactive labelled nucleic acid sequence comprising a fragment of the DNA coding for said polypeptide is used for hybridization. Alternatively they are detected by immunological screening using monoclonal antibodies, such as Mab-135 and Mab-176.

Modification of the coding or non-coding region of the hybrid vector is achieved e.g. by methods described hereinbefore, e.g. under 1d).

The invention further relates to the use of the polypeptides of the invention with IgE binding activity for the treatment or prevention of allergic conditions in patients being allergic against all kinds of antigens, for example pollens, cat danders, house dust mites, and the like. Particularly important would be the treatment of high risk patients during critical periods, including especially high risk new-borns which are not breast-fed. The polypeptides of the present invention are administered enterally, for example nasally, rectally or orally, or parenterally, for example, intramuscularly, subcutaneously or intravenously, usually in dosage unit forms such as tablets, dragées, ampoules, vials, or suppositories. The amount of the polypeptide to be administered depends on its specific activity, on the weight and general condition of the patient, the severity of the disease, the mode of administration and has to be based on the judgement of the physician. In general a dose of between about 100 μg and about 5000 μg per kg bodyweight and day may be administered.

The invention further relates to pharmaceutical preparations containing the polypeptides of the invention having IgE-binding activity in an antiallergically effective amount optionally in conjunction with conventional pharmaceutically acceptable carriers that are suitable for oral, rectal, nasal or parenteral, i.e. intramuscular, subcutaneous or intraperitoneal, administration and that do not deleteriously interact with the active ingredients.

There are suitable tablets, capsules, vials containing a solid powder, or nebulizers, sprays, vials, ampoules and the like containing infusion solutions, preferably aqueous solutions or suspensions, it being possible to prepare these before use, for example from lyophilized preparations that contain the active ingredient alone or together with a carrier, such as mannitol, lactose, glucose, albumin and the like. The pharmaceutical preparation may be sterilized and, if desired, mixed with adjuncts, for example preservatives, stabilisers, emulsifiers, solubilisers, buffers and/or salts for regulating the osmotic pressure. Sterilization can be achieved by sterile filtration through filters of small pore size (0.45 μm diameter or smaller) after which the preparation can be lyophilized, if desired. Antibiotics may also be added in order to assist in preserving sterility.

The pharmaceutical preparations according to the present invention are dispensed in unit dosage forms, for example ampoules, comprising 1 to 2000 mg of a pharmaceutically acceptable carrier per unit dosage and about 1 to 100 mg, preferably about 2 to 50 mg, of the active ingredient per unit dosage.

The invention also relates to a method for producing a pharmaceutical preparation characterized in that a polypeptide of the invention is admixed with a pharmaceutically acceptable carrier.

The pharmaceutical preparations are produced in a manner known per se, for example by conventional mixing, dissolving, lyophilizing and the like processes and contain from about 0.1% to 100%, especially from about 1% to 50% of the active substances.

The use of the new polypeptides of the invention for the prophylactic and therapeutic treatment of the human body is also an object of the present invention.

The abbreviations used throughout the description have the following meanings:
bp—base pairs
BSA—Bovine serum albumin
cDNA—complementary DNA
cpm—counts per minute (radioactive decay)
dA—2'-deoxyadenosine
dATP—2'-deoxyadenosine triphosphate
dC—2'-deoxycytidine
dCTP—2'-deoxycytidine triphosphat
dG—2'-deoxyguanosine
dGTP—2'-deoxyguanosine triphosphate
dT—2'-deoxythymidine
dTTP—2'-deoxythymidine triphosphat
DNA—deoxyribonucleic acid
dNTP—mixture of dATP, dCTP, dGTP and dTTP
ds—double-stranded
DTT—1,4-dithiothreitol
EDTA—ethylendiaminetetraacetic acid disodium salt
FCS—fetal calf serum HAT—hypoxanthine/aminopterin/thymidine
HBSS—Hank's balanced salt solution
HT—hypoxanthine/aminopterin
Hepes—N-2-hydroxyethylpiperazine-N'-2-ethensulfonic acid
IgE—immunoglobulin E
mRNA—messenger RNA
min—minutes
PBS—phosphate buffered physiological saline
Pipes—piperazine-N,N'-bis(2-ethanesulfonic acid)
PMSF—phenylmethylsulfonyl fluoride
RIA—radioimmuno assay
RNA—ribonucleic acid
rpm—revolutions per minute
SDS—sodium dodecyl sulfate
ss—single-stranded
Tris—tris(hydroxymethyl)aminomethane
tRNA—transfer RNA
μg—microgram The following examples serve to illustrate the present invention but should not be construed as a limitation thereof.

EXAMPLES

The following buffer solutions and media are used:

| | |
|---|---|
| agar | LB-broth suplemented with 2% agar |
| elution-buffer | 10 mM Tris-HCl, pH 7.5, 1 mM EDTA, 0.2% SDS. |
| LB-broth | 1% Bacto-tryptone (Difco), 0.5% Bacto yeast extract (Difco), 170 mM NaCl, adjusted to pH 7.5 with NaOH |
| lysis-solution | 0.5M NaOH, 1.5N NaCl |
| HBSS | 8 g NaCl, 400 mg KCL, 48 mg $Na_2HPO_4$, 350 mg $NaHCO_3$, 60 mg $KH_2PO_4$, 100 mg phenolred in 1 liter $H_2O$ |
| HBSS-FCS | HBSS supplemented with 10% FCS, 0.01% $NaN_3$, 66 mM Tris-HCl pH 7.2 |
| HT-medium | RPMI/c-medium supplemented with 40 μl 2-mercaptoethanol, 100 μM hypoxanthine, 1 μM thymidine |
| HAT-medium | HT-medium supplemented with 10 μM aminopterin |
| MBS-H | 88 mM NaCl, 1 mM KCl, 0.33 mM $Ca(NO_3)_2$, 0.41 mM $CaCl_2$, 0.82 mM $MgSO_4$, 2.4 mM $NaHCO_3$, 10 mM Hepes (pH 7.4) |
| Mc Conkey agar | 50 g of premixed McConkey agar (Becton Dickinson) per one liter of destilled water |
| oocytes lysis-puffer | 20 mM Tris-HCl pH 7.5, 50 mM NaCl 0.5% Triton X 100, 0.5% sodium deoxycholat, 0.1% methionin, 1 mM PMSF |
| PBS | 1 liter contains 8 g NaCl, 0.2 g KCl, 1.44 g $Na_2HPO_4.2H_2O$, 0.2 g $KH_2PO_4$ |
| RPMI 1640-medium | available from Gibco |
| RPMI 1640/c-medium | RPMI 1640-medium supplemented with 1% penicillin-streptomycine (Gibco), 1% L-glutamine (Gibco) and 15% (v/v) FCS (Gibco) |
| RVT-buffer | 200 mM Tris-HCl, pH 8.3 at 42° C., 20 mM $MgCl_2$, 280 mM KCl, 20 mM DTT |
| SOC-medium | 2% Bacto Tryptone (Gibco), 0.5% Yeast-Extract (Gibco), 10 mM NaCl, 2.5 mM KCl, 10 mM $MgCl_2$, 5 mM $MgSO_4$, 20 mM Glucose |
| SSC-buffer | 15 mM sodium citrate, 150 mM NaCl, |
| TBE-buffer | 1 liter contains 10.8 g Tris, 5.5 g boric acid, 4 ml 0.5 ml EDTA (pH 8.0) |
| TE-buffer | 10 mM Tris-HCl pH 7.5, 1 mM EDTA |
| TNE-buffer | 10 mM Tris-HCl 1 mM EDTA, 0.1M NaCl, adjusted to pH 7.8 with NaOH |
| wash-buffer | 10 mM Tris-HCl pH 7.5, 1 mM EDTA, 0.5M NaCl, 0.2% SDS. |

USE OF RESTRICTION ENZYMES AND ISOLATION OF DNA

All restriction enzymes are used in the buffer conditions as recommended by the supplier on the enzyme data sheet. In general, 3 Units of an enzyme are used to digest 1 μg of DNA. The incubations are left for 2 hours at 37° C. To stop the enzymatic reaction EDTA and Na-acetate are added to final concentrations of 15 mM and 200 mM, respectively. To extract the DNA one volume of a 1:1 mixture of chloroform/phenol, presaturated with TNE, is added and the mixture shaken vigourously. Organic and aqueous phase are separated by centrifugation at 5000 g for 5 min (room temperature). The aqueous phase is transferred to a new tube and extracted with 1 volume of chloroform. After centrifugation, the DNA is precipitated by the addition of 2.5 volumes of ethanol. The sample is incubated at least 2 hours at −20° C. and centrifuged at 10000 g for 10 minutes. The DNA pellet is washed once with 70% ethanol, dried for 10 minutes in a vacuum dessicator and finally dissolved in the appropriate volume of TE buffer.

The following strains are used
E. coli strain HB101
$F^{31}$, hsdS20 ($r^-\beta$, $m^-B$), recA13, ara14, proA2, lacY1, galK2, rspL20(Sm'), xyl-5,mtl-1,supE44,$\lambda^-$. (Boyer and Rouland-Dussoix 1969; Bolivar and Backman 1979).

RPMI 8866 cell-line

RPMI 8866 cells (ATCC No. CCL 107) are from a lymphoblastoid B cell line expressing receptors for IgE. The cell line was recieved from Dr. P. Ralph, Sloan-Kettering Research Institute, NY, USA.

The following plasmids are used pUC-9

Available from Pharmacia, P-L Biochemicals Upsalla, Sweden. The pUC-9 plasmid consists of a pBR322 derived ampicillinase gene and an origin of DNA replication ligated to a portion of the lac Z gene of E. coli. A DNA insert containing an array of unique restriction enzyme recognation sites has been introduced in the lac Z region of this plasmid.

pUC-KO

This plasmid is a derivative of pUC-9 in which the promoter/operator region of the lac Z gene is deleted between the HaeII restriction site just outside the promoter sequence and the HindIII restriction site, within the polylinker, leaving the other sequences of the pUC-9 plasmid unchanged.

pGEM ™ -1

Available from Promega Biotec, Madison, USA. This plasmid is a special transcription vector. It was constructed using the bacteriophage SP6 promotor-containing plasmid pSP64 (Melton, D. A., et al. (16) and a bacteriophage T7 promotor. The resulting plasmid has two opposed promotors SP6 and T7, separated by a short piece of DNA containing multiple cloning sites.

pIN-III-ompA plasmids

Described by Gharayeb et al. (13). These plasmids are special secretion cloning vectors in E. coli. The secretion of a cloned gene product across the cytoplasmic membrane can be achieved by fusing appropriate signal peptides to the amino-terminal end of the gene product. In these plasmids the DNA fragment coding for the signal peptide of the ompA protein, a major outer membrane protein of E. coli, has been inserted into a high-level expression vector. A foreign DNA fragment can be cloned in any one of the three reading frames at the unique EcoRI, HindIII or BamHI sites immediately after the ompA signal peptide coding sequence. The pIN-III-ompA-plasmids of the type 1, 2 and 3 trigger different reading frames for translation.

EXAMPLE 1

Isolation of mRNA from RPMI 8866 Cells

RPMI 8866 cells are grown in tissue culture flasks (Falcon, 175 cm$^2$) with 50 ml RPMI 1640 medium supplemented with 15% FCS, 100 units/ml penicillin and 100 $\mu$g/ml streptomycin. The cells from 50 confluent flasks (approximate 10$^8$ cells/flask) are collected by centrifugation and washed once with 50 ml PBS. The cell pellet (5 g) is dissolved in 25 ml of a solution prepared from 100 g of guanidinium thiocyanate, 100 ml of H$_2$O, 10.6 ml 1M Tris-HCl, pH 7.5, 4.2 ml 0.5M EDTA, 21.2 ml 20% N-laurylsarcosine and 2.1 ml of 2-mercaptoethanol. The cell lysate is homogenized in an omnimixer for 90 seconds at full speed. Two volumes of a 1:1 mixture of chloroform and phenol are added. The mixture is shaken vigorously for 1 min and then centrifuged at 5000 g for 10 min in a Sorvall centrifuge at 10° C. The aqueous phase is recovered and the extraction repeated 4 more times. Two volumes of ethanol are added to the aqueous phase. The precipitate is recovered by chilling to −20° C. for 15 minutes, followed by centrifugation at 10 000 rpm at 4° C. in a Sorvall SS34 rotor for 10 minutes. The pellet is dissolved in 4 ml of TE buffer. 7.5 g of baked CsCl (Merck) and 50 $\mu$l of 0.1N HCl are added and the solution adjusted to 7.5 ml and layered onto a 2 ml cushion of 5.7M CsCl in a 12 ml centrifuge tube. The tube is filled up with H$_2$O and centrifuged for 16 h at 29000 rpm 20° C. in a TST 41 rotor (Knotron). At the end of the run most of the supernatant is removed and the tube is drained by quickly inverting. The glazy RNA pellet is dissolved in 1 ml of TE buffer and 0.2% SDS by vortexing and occasional warming (2 minutes) at 37° C. The RNA is precipitated with ethanol as described by Maniatis et al. (1) p. 461–462. The dried mRNA is dissolved in 1 ml of elution buffer. After heating for 2 min at 68° C. and chilling on ice, 130 $\mu$l of 5M NaCl are added and the solution is applied to a 2 ml column of oligo-dT cellulose (2 ml bed volume in a 5 ml syringe type 7, P-L Biochemicals) equilibrated in wash buffer. After two subsequent applications of the sample the column is washed with 15 ml of wash buffer, and the bound mRNA eluted with 4 ml of elution buffer. The eluted material is heated for 2 min at 68° C., chilled on ice and 0.44 ml of 5M NaCl are added. The solution is applied two times to the re-equilibrated oligo-dT cellulose column. After washing with 15 ml of wash buffer the bound mRNA is eluated with 4 ml of elution buffer. The recovery of mRNA is determined by measuring the absorbance at 260 nm (OD$_{260 nm}$=1 is according to a concentration of 40 $\mu$g/ml). The mRNA (150 $\mu$g) is ethanol-precipitated. The precipitate is collected by centrifugation (15 min at 16000 g), dissolved in 0.4 ml H$_2$O and re-precipitated with ethanol. The mRNA-pellet is air dried and dissolved in 150 $\mu$l of TE buffer supplemented with 0.1% SDS.

EXAMPLE 2

Enriching mRNA Coding for IgE-Receptor and IgE-BF Related Polypeptides

130 $\mu$g of polyA-mRNA from Example 1 (1 $\mu$g/$\mu$l) are heated for 5 min at 70° C., chilled on ice and loaded onto 12 ml of a 5–20% linear sucrose gradient in 0.1M NaCl, 10 mM Tris-HCl pH 7.5, 1 mM EDTA and 0.5% SDS. The gradient is centrifuged for 5 hours at 41'000 rpm in a TST 41 rotor at 25° C. 30 fractions (volume 0.4 ml/fraction) are collected and assayed by injection into oocytes of Xenopus laevis, as described in Example 3.

EXAMPLE 3

In Vivo Translation of mRNA in Xenopus Laevis Oocytes

Adult male and female Xenopus laevis can be obtained from a variety of animal suppliers, including K. Evans (716 Northside, Ann Arbor, MI 48105). The frogs can be kept in any type of water tank, without aeration, at 18°–22° C. Regular feeding (twice per week) with fragments of beef liver and beef heart will help maintain a healthy colony. Oocytes should be obtained from healthy, adult, femal Xenopus. This is easily accomplished by anesthetizing the frog in a 1:1000 (w/v) solution of ethyl m-aminobenzoate in water for 10–30 minutes. A small incision (1 cm) on the posterior ventral side gives ready access to the frog's ovary. After removing a segment of the ovary, the incision can be sutured, and the frog will quickly recover in water. The ovary should be placed immediately in modified Barth saline (MBS-H) and individual oocytes are stripped away with a platinium loop. Large, fully grown oocytes are injected using a fine micropipette, a micrometer syringe, and any standard dissecting stereomicroscope. The construction of a suitable injection pipette is described by Gurdon (18). Oocytes are placed on a microscope slide, blotted dry with a paper towel, and the slide is then placed on the microscope stage. Before and during the insertion of the pipette, the oocytes can be positioned with blunt watchmaker's forceps. After the pipette has penetrated the oocytes, a 30–50 nl aliquote of the mRNA solutions (1 mg/ml) of Example 2 is delivered using the micrometer syringe. Groups of 40 eggs containing the mRNA of the same fraction are incubated in 0.5 ml Barth solution, supplemented with 6% FCS, for 45 h at 20° C. The incubation medium is removed and the oocytes are homogenized in 900 μl of oocyte lysis buffer. The homogenate is centrifuged in an Eppendorf centrifuge for 10 minutes. The upper phase is recovered and aliquots of 50 μl tested in a RIA, as described in Example 7.

EXAMPLE 4

Preparation of Hybridoma Cells Producing Monoclonal Antibodies Against $Fc_\epsilon R$ BALB/c mice are immunized by three intraperitoneal injections of $5\times10^7$ viable RPMI 8866 cells in PBS at 4 week intervals. Individual mouse serum samples collected 2 days after the last injection are tested for anti-$Fc_\epsilon R$ activity. Spleen cells from two animals displaying the highest titers are pooled and used for fusion the next day. The spleens are teased and for each fusion, $1\times10^8$ washed spleen cells are pelleted with $25\times10^6$ NSI/1-Ag4/1 mouse myeloma cells (obtained from the American type tissue culture collection) for 5 min at $350\times g$. The cellular pellet is gently resuspended for 30 sec in 2 ml polyethylene glycol solution (PEG-1540, Baker) consisting of 20 g PEG dissolved in 28 ml RPMI 1640 medium (Gibco) containing 15% (v/v) dimethylsulfoxide.

8 ml of RPMI/c medium is added dropwise over a period of 90 sec followed by the rapid addition of an additional 5 ml. The cellular suspension is mixed by inverting the tube, allowed to stand for 2.5 min and centrifuged at $350\times g$ for 5 min. The pellet is resuspended in 5 ml RPMI/c medium and 50 μl aliquots are dispensed into each well of 4 Costar #3596 24-well plates also containing $1\times10^6$ normal BALB/c spleen cells in 1 ml HAT-medium. All cultures are maintained by alternate addition or replacement of HAT medium every few days as required, starting on the 5th day following fusion. After 14 days HAT is replaced by HT medium and after 28 days by RPMI/c. Supernatants of individual wells (192 cultures) are screened for anti-$Fc_\epsilon R$ antibodies one and two weeks after the fusion. 21 cultures producing the desired antibodies are cloned by limiting dilution; they are diluted in RPMI/c to a concentration of 10 viable cells/ml and 50 μl aliquots of these suspensions are placed into wells of 96-well plates (Linbro #76-003-05, Flow Labs), containing 100 μl HT medium and $1\times10^5$ normal BALB/c spleen cells. The wells are examined microscopically to ensure that the growing cultures are monoclonal. Samples of supernatants taken therefrom are tested for antibody activity; positive cultures are selected and expanded in larger culture vessels. 14 monoclonal cell lines secreting antibodies of the required specificity are finally obtained. Three clones, named 207.25.A.4.4/45, 208.25A.4.3/135 and 208.25D.2.1/176, deposited at the Collection Nationale de Cultures de Microorganismes of the Institut Pasteur, Paris, available under accession No. I-452, I-425 and I-420, respectively, are herein used. The monoclonal antibodies produced thereby are designated Mab-45, Mab-135 and Mab-176.

EXAMPLE 5

Isolation and Purification of Monoclonal Antibodies

Balb/c mice are pretreated intraperitoneally with 0.5 ml pristane (Aldrich). 2 weeks later, $5\times10^6$ cloned hybridoma cells of Example 4 are injected intraperitoneally. After 8–10 days ascites fluid is collected, centrifuged at $800\times g$ and stored at $-20°$ C. Defrosted ascites fluid is centrifuged at $50,000\times g$ for 60 min. A fat layer floating on the surface is carefully removed, and the protein concentration is adjusted to a concentration of 10–12 mg/ml. Crude immunoglobulin is precipitated by dropwise addition of 0.9 volume equivalents of saturated ammonium sulphate at 0° C., then dissolved in 20 mM Tris-HCl/50 mM NaCl (pH 7.9) and dialyzed against the same buffer. An immunoglobulin G fraction is obtained by DEAE-D52 cellulose (Whatman) chromatography using a buffer gradient system of 20 mM Tris-HCl/25–400 mM NaCl, pH 7.9.

EXAMPLE 6

Preparation of $^{125}I$ Labelled Antibody Mab-135

40 μg Mab-135 (PBS solution of Example 5) are iodinated with 0.5 mCi $^{125}I$ sodium iodide and chloramine T following the general procedure of F. C. Greenwood et al. (19). The solution containing iodinated Mab-135-protein is dialysed 4 times, 6 hours each, against 1 liter of PBS-puffer. The final product has a specific activity of approximately $2\times10^7$ cpm/μg protein. $^{125}I$ labelled antibody Mab-176 is prepared similarly.

EXAMPLE 7

Radioimmunoassay for the Detection of IgE-BF in Cell Supernatants and Serum

Wells of polyvinyl chloride microtiter plates are incubated overnight at room temperature with 150 μl of 0.01M carbonate buffer, pH 9, containing 5 μg/ml of Mab-176 of Example 5. The plates are then washed once with PBS and reacted for 2 hrs at room temperature with 200 μl Hanks' balanced salt solution containing 10% fetal calf serum (HBSS-FCS), then again washed 10 times with PBS and incubated with 100 μl of test sample for 8 hrs at room temperature. The blank is determined by using HBSS-FCS. The plates are washed 10 times with PBS and incubated overnight at room temperature with 100 μl per well of $^{125}I$-Mab-135 (2 to $4\times10^5$ cpm in HBSS-FCS, Example 6), then washed 10 times with PBS and counted in a gamma counter.

EXAMPLE 8

Synthesis of ss-cDNA from mRNA

12 μl (0.5 mg/ml) of the mRNA solution of Example 2 showing the highest binding capacity for $^{125}I$-Mab-135, detected in the RIA of Example 7, is added to 25 μl RVT buffer, 2.5 μl dNTP mix (20 mM of dATP, dTTP and dGTP each), 5 μl of 1 mg/ml oligo-$dT_{12-18}$ (P-L-Biochemicals), 1 μl α-$^{32}$P-dCTP (10 μCi, 3000 Ci/mmol), 3 μl RNasin TM (60 units, Promega Biotec, Madison, U.S.A.) and 3 μl reverse transcriptase (66 units, Promega Biotec.). Radioactive dCTP is included in the reaction mixture to facilitate the recovery and the determination of the yield of the cDNA in all following steps of the synthesis. The mixture is incubated for 1.5 h at 42° C. The reaction is stopped by addition of 2 μl 0.5M EDTA pH 7.5. The mRNA is degraded by addition of 25 μl 0.15M NaOH and incubation at 45° C. for 1 h. The solution is neutralized by addition of 25 μl 1M Tris-HCl (pH 8.0) and 6 μl 1M HCl. 2 μl of 20% SDS are added and the solution is extracted with 0.15 ml phenol-chloroform mix (equal volumes of phenol and chloroform equilibrated with TNE buffer). The aqueous phase is applied to a 2 ml Sephadex ® G-50 column in a pasteur pipet equilibrated with TNE buffer, in order to separate the newly synthesized cDNA from the unincorporated nucleotides and the degraded mRNA. Twelve fractions of 200 μl each are collected and the radioactivity in each fraction determined approximately with a Geiger counter. The first three fractions containing radioactivity are pooled. 1.9 μg of ss-cDNA is recovered, and ethanol-precipitated as described by Maniatis et al. (1), p. 461–462. The ss-cDNA is dissolved in 20 μl H$_2$O.

EXAMPLE 9 ds-cDNA-Synthesis and S1-Digestion

The obtained ss-cDNA is incubated in 100 μl final volume of 100 mM Hepes, pH 6.9, 10 mM MgCl$_2$, 2.5 mM DTT, 70 KCl, 0.5 mM of each dNTP (dATP, dCTP, dTTP, dGTP), and 20 units of DNA polymerase I large fragment, Klenow enzyme (Boehringer Mannheim) for 3 hours at 15° C. Then another 20 units of the same enzyme are added and the incubation is continued for 10 hours at 15° C. The reaction is terminated by adding EDTA to 20 mM. The mixture is extracted with phenol-chloroform and precipitated with ethanol as described by Maniatis et al. (1), p. 461–462 and 458–459. The resulting ds-cDNA is treated in a 100 μl incubation mixture containing 250 mM NaCl, 50 mM sodium acetate pH 4.5, 1 mM ZnSO$_4$, 200 units of S1 nuclease (Boehringer, Mannheim) at 30° C. for 30 minutes. The reaction is stopped by adding EDTA to 25 mM. After adding 1M Tris-HCl, pH 8.0 to 100 mM and SDS to 1%, the reaction is extracted with phenol/chloroform and passed through a Sephadex G-200 column in a pasteur pipette and 2 ml of volume, equilibrated with TNE buffer. Fraction containing ds-cDNA are determined by measuring radioactivity, pooled, precipitated with ethanol and dissolved in 15 μl H$_2$O. 3.2 μg of ds-cDNA are obtained.

EXAMPLE 10

3'-Oligo(dG)-Tailing of pUC-KO Plasmid

20 μg of pUC-KO plasmid are cut with 50 units of PstI (Boehringer, Mannheim) in 200 μl of 50 mM Tris-HCl pH 8.0, 10 mM MgCl$_2$ and 50 mM NaCl. EDTA is added to 20 mM and the reaction mixture extracted with an equal volume of chloroform/phenol (1:1). The cut plasmid-DNA is precipitated by the addition of 2.5 volumes of ethanol and recovered by centrifugation at 10000 g for 10 minutes. The supernatant is discarded and the pellet is dissolved in 50 μl H$_2$O. The probe is incubated in 150 μl of a solution containing 200 mM potassium cacodylate pH 6.9, 1 mM CoCl, 2 mM DDT, 10 μM dGTP and 80 units of terminal deoxynucleotidyl transferase (Pharmacia P-L Biochemicals, Upsalla Sweden) for 5 minutes at 37° C. To stop the reaction, EDTA is added to 10 mM and the mixture extracted once with phenol/chloroform (1:1). The DNA is precipitated with ethanol and recovered by centrifugation at 10000 g. The DNA pellet is dissolved in 200 μl of TE buffer and loaded onto a horizontal 0.8% agarose gel in TBE buffer using a slot with a width of 3 cm. After electrophoresis for 16 hours at 1 V/cm, the DNA is recovered by electroelution at 5 V/cm for 20 min and recovered from the bag by vigorous pipetting. The DNA is phenol-chloroform extracted and ethanol-precipitated as described in Example 1. After centrifugation the DNA is dissolved in TE buffer and stored at −20° C.

EXAMPLE 11

Preparation of a Plasmide Containing ds-cDNA Coding for IgE-Receptor Related Polypeptide and Transformation of E. coli HB101 therewith 800 ng ds-cDNA of Example 9 are incubated in 40 μl of a solution containing 200 mM potassium cacodylate, pH 6.9, 1 mM CoCl$_2$, 2 mM DTT, 100 pmol $^3$H-dCTP, and 12 units of terminal deoxynucleotidyl transferase (P-L Biochemicals) for 5 minutes at 37° C. To stop the reaction, EDTA is added to 10 mM. The mixture is extracted with phenol/chloroform, and the DNA precipitated with ethanol. The dC-tailed ds-cDNA is dissolved in H$_2$O and stored at −20° C. A mixture of 50 ng dC-tailed ds-cDNA and 150 ng dG-tailed pUC-KO of Example 10 in 200 μl TNE buffer is incubated for 5 min at 65° C., 60 min at 55° C. and then cooled slowly to 30° C. in a water bath over a period of 3-5 hours. 2 μl aliquots of this annealing mixture are added to 200 μl of competent E. coli HB101, which have been prepared for transformation by treatment with calcium chloride as described by Maniatis et al. (1), p. 250. The mixtures are kept on ice for 30 minutes and heated to 42° C. for 2 min, then diluted with 1 ml of SOC-medium and incubated at 37° C. for 1 h. The content of 10 tubes is pooled and the cells are collected by centrifugation at 2000 g for 5 min. Each cell pellet is resuspended in 1 ml of SOC-medium and spread on a 10 cm agar plate containing LB-medium and 50 μg/ml ampicillin. The plates are incubated at 37° C. for 16 h. About 5000 transformed colonies are obtained, characterized by their ampicillin resistance.

EXAMPLE 12

Identification of Clones Containing ds-cDNA Coding for Human IgE-Receptor and IgE-Binding-Factor Related Polypeptide by Hybrid-Selected Translation Individual colonies of Example 11 are grown to saturation in 2 ml LB-broth, containing 100 μg/ml ampicillin. 96 cultures are pooled and the plasmid-DNA is isolated using the alkaline lysis method (Maniatis, T. et al., p. 90 (1)) 100 μg of alkali denaturated plasmid-DNA are covalently bound to 50 mg of activated ATP-cellulose prepared by the method of Seed (20).

PolyA-mRNA (60 μg) from RPMI 8866 cells (Example 1) is dissolved in 300 μl of 15 mM Pipes pH 6.4, 1.5 mM EDTA, 600 mM NaCl, 0.2% SDS, 50% formamide and hybridized to the cellulose-bound plasmid-DNA at 37° C. for 16 hours with gentle agitation. The cellulose is washed 10 times in 50% formamide, 45 mM NaCl, 4.5 mM sodium citrate, 20 mM Pipes pH 6.4 and 1 mM EDTA. The hybridized mRNA is eluted from the cellulose by incubating twice at 65° C. for 2 minutes in 100 μl 90% formamide, 0.2% SDS, 10 mM Pipes 6.4, 5 mM EDTA, 20 μg/ml calf liver tRNA. The eluted mRNA is ethanol precipitated twice. The precipitated polyA-mRNA obtained from each pool is dissolved in 6 μl water and used for injection into Xenopus laevis oocytes and analysed as described in Examples 3. The translated proteins are screened in the RIA as described in Example 7. Of ten pools with 96 colonies each, one is positive. These 96 colonies are combined to 12 new pools of 8 colonies and screened in the same way. Finally, a single colony is identified of which the protein gives a positive signal in the RIA after the translation of the mRNA in frog oocytes. The clone is expanded in LB-broth containing 100 μg/ml ampicillin. The plasmid-DNA is isolated from this colony. 1 μg of the plasmid DNA is digested with the restriction enzyme PstI, an enzyme which cleaves at both boundaries between the vector DNA and the ds-cDNA insert, and the sequence of the cDNA insert is determined end to end using the dideoxy chain termination sequencing method of Sanger et al. (21). The sequencing is done as described in detail in the Amersham handbook "M13 cloning and sequencing" using the reagents included in the sequencing kit (Amersham, N 4501 and N4502). The ds-cDNA insert is 417 bp long and its sequence is shown in Formula II between bp no. 878 and bp no. 1295. This ds-DNA coding for the C-terminal part of IgE-receptor and IgE-binding-factor is used as DNA probe to screen by hybridization for a longer cDNA clone containing all the coding information for the polypeptides related to human IgE-receptor or IgE-binding factor.

EXAMPLE 13

Cloning of a cDNA Containing the Complete Coding Sequence for the Human IgE-Receptor The polyA-mRNA is isolated from RPMI 8866 cells as described in Example 1. The first steps of cDNA synthesis are done according to Example 2-8. Then, the protocol is changed in order to enrich for full length ds-cDNA. The ss-cDNA is dissolved in 32 μl H$_2$O. The ss-cDNA is extended with oligo-dC tails in a reaction mixture containing 32 μl ss-cDNA (2.8 μg), 10 μl 1M potassium cacodylate, pH 7.0, 5 μl 10 mM CoCl$_2$, 5 μl 1 mM DTT and 1 nmol of dCTP. After preincubation for 5 min at 37° C., 3 μl of terminal deoxynucleotidyl transferase (81 units, P-L Biochemicals) are added and incubation is allowed to proceed for 10 min. 50 μl of TNE buffer are added and the ss-cDNA is chloroform/phenol-extracted and ethanol-precipitated. The pellet is washed with 70% ethanol, air-dried and dissolved in 15 μl of H$_2$O, 25 μl RVT buffer, 2.5 μl dNTP mix (20 mM of dATP, dTTP and dGTP each) and 5 μl 0.2 mg/ml oligo dG$_{12-18}$ (P-L Biochemicals). 3 μl of reverse transcriptase (66 units, Promega Biotec) are added and the mixture is incubated at 42° C. for 90 minutes. The reaction is stopped by addition of 2 μl 0.5M EDTA, pH 7.5 and 50 μl TNE buffer, and the mixture is extracted with 0.15 ml phenol-chloroform (1:1). The aqueous phase is applied onto a Sephadex ® G50 column (2.5 ml in TNE buffer) and the breakthrough fraction (0.4 ml) containing 1.1 μg of ds-cDNA is collected. The ds-cDNA is ethanol-precipitated. The resulting pellet is taken up in 32 μl H$_2$O and the ds-cDNA extended with radioactive labelled oligo-dC tails as described in Example 11. The reaction is stopped by addition of 1 μl 0.5M EDTA, pH 7.5, and the sample loaded onto a horizontal 1% agarose gel in TBE buffer using slots with a width of 0.5 cm. In a parallel slot, 1 μg of bacteriophage lambda DNA (digested with EcoRI and HindIII) is loaded to serve as a size marker. After electrophoresis for 2 h at 2.5 V/cm, the gel is soaked in TBE buffer containing 0.5 μg/ml ethidium bromide in order to stain the ds-DNA. The region containing ds-cDNA with approximate size between 1.4 and 2 kilobases is excised and placed in two micro-collodium bags (Sartorius) presoaked in H$_2$O. 0.3 ml H$_2$O are added and the bags are placed in a horizontal electrophoresis apparature (Bio-Rad) containing half-concentrated TBE buffer. The ds-cDNA is electroeluted at 5 V/cm for 20 min and recovered from the bag by vigorous pipetting. The ds-cDNA is phenol-chloroform extracted and ethanol-precipitated. After centrifugation the ds-cDNA is dissolved in 100 μl TNE buffer. 100 ng of ds-cDNA are recovered (determined from the yield of radioactivity).

EXAMPLE 14

Annealing of dG-Tailed pUC-KO with Poly(dG) Tails to ds-cDNA with Poly(dC) Tails and Transformation of E. coli with the Obtained Plasmid 40 μl ds-cDNA (40 ng of size-fractionated material of Example 13) is mixed with 16 μl (200 ng) of oligo-dG$_{10-20}$ tailed pUC-KO plasmid-DNA from Example 10 and 194 μl TNE buffer and sequentially incubated at 65° C. for 10 min, at 46° C. for 1 h and at room temperature for 1 h. The annealed DNA is used to transform competent E. coli HB101 cells (strain LM 1035), which have been prepared for transformation as described in Example 11. Aliquots of 2 μl of the annealing mixture are added to parallel tubes containing 200 μl of competent cells. The tubes are left on ice for 30 min. After a heat shook of 90 sec at 42° C. and chilling in ice for 2 min, 0.8 ml of SOC medium is added per tube which is then incubated for 60 min at 37° C. After the incubation the content from 10 tubes is pooled. The cells are collected by centrifugation at 2000 g for 5 min and plated on McConkey agar plates (15 cm of diameter) containing 100 μg/ml ampicillin. The plates are incubated overnight at 37° C. Approximately 1000 ampicillin resistent colonies are obtained per plate. They are lifted onto nylon membranes (Pall-Biodyne, Glen Cove, New York-U.S.A.) and the membranes are laid on McConkey agar plates with the colonies facing upwards. After incubation for 5 hours at 37° C., two replicas are made onto nylon membranes. The master membrane is stored at 4° C. on an agar plate. The replicas are processed for colony hybridization by successively placing them on 3 MM paper (Whatman Ltd., Maidstone, U.S.A.) saturated with 0.5M NaOH, 1.5M NaCl for 5 minutes and with 0.5M Tris-HCl, pH 8.0, 1.5M NaCl for 10 minutes. Between each incubation filters are blotted on dry Whatman 3 MM filters. The replica filters are baked at 80° C. in a vacuum oven for 2 hours and immediately used for DNA hybridization.

EXAMPLE 15

Filter Hybridization

The cDNA insert from 10 μg plasmid coding for part of the IgE-receptor obtained from the positive clone of Example 12 is prepared by digestion with PstI restriction endonuclease. The cDNA insert (450 bp) is separated from pUC-KO vector DNA (2900 bp) by electrophoresis through a 1.5% agarose gel in TBE buffer and recovered by electroelution and ethanol precipitation as described in Example 13. The pure cDNA insert (200 ng) is rendered radioactive using a nick translation system from Amersham (N.5000) following the instructions given by the supplier. The radioactive labelled cDNA probe has a specific activity of $5 \times 10^8$ dpm/μg. The radiolabelled cDNA is denatured by incubation at 95° C. for 10 minutes and immediately chilled on ice. The replica filter of Example 14 are prehybridized in a sealed plastic bag for 2 h in 100 ml of a solution containing 0.9M NaCl, 0.18M Tris-HCl, pH 8.0, 6 mM EDTA, 0.02% Ficoll 400, 0.02% polyvinylpyrrolidone, 0.02% BSA, 0.2% SDS and 50 µg/ml of denatured calf thymus DNA. The hybridization is performed over night in a sealed plastic bag containing 5 ml of the same solution supplemented with the heat-denatured radioactive labelled cDNA insert from above. After hybridization the filters are washed in 2×SSC/0.2% SDS, followed by three washes at 65° C. with 200 ml of 0.2×SSC/0.2% SDS. The filters are dried and exposed to a Kodak X-ray film (XAR-5) over night. The filters are marked with radioactive ink to allow the alignment of the filters with the autoradiogram. Two positive clones are found, the DNAs of which hybridize to the radioactive labelled DNA fragment coding for IgE-receptor. They are named pCL-1 and pCL-2.

EXAMPLE 16

Isolation and Analysis of pCL1- and pCL2-DNA

The pCL1 and pCL2 clones are grown up and their plasmid DNAs are isolated using the alkaline lysis method (Maniatis, T., et al. (1), p. 90). The DNA is digested with PstI, an enzyme which cuts the cDNA at the boundaries between the vector DNA and the DNA inserts. The fragments are separated by electrophoresis and the complete cDNA inserts isolated by electroelution as described in Example 13. The cDNA inserts of these two plasmids are sequenced end to end using the method of Sanger et al. (21) described in detail in the Amersham handbook. A summary of the restriction and sequence analysis is given in FIG. 2 and Formula II.

EXAMPLE 17

Transfer of the IgE-Receptor Related cDNA into a Plasmid Suitable for Transcription 10 µg of the pCL-2 plasmid DNA are digested with the restriction enzymes PstI and HincII (Boehringer Mannheim). The 1.5 kb cDNA insert and the 2.9 kb plasmid vector DNA are separated on a 1% agarose gel in TBE buffer using a slot width of 3 cm. After electrophoresis for 16 hours at 1 V/cm, the DNA is recovered by electroelution as described in example 13. In parallel, 10 µg of the plasmid pGEM TM -1 is digested with PstI and HincII, extracted once with phenol/chloroform and precipitated with ethanol. 10 ng of the 1.5 kb cDNA insert and 10 ng of the PstI cleaved pGEM TM -1 are ligated in a volume of 10 µl for 4 hours at 15° C. The reaction mixture contains in addition 10 Tris-HCl pH 7.5, 10 mM MgCl2, 2 mM DTT, 0.1 mM ATP and 100 units T4 ligase (Boehringer Mannheim). 5 µl of the mixture are used to transform competent E. coli HB101 (strain LM 1035) as described by Maniatis et al. (1), p. 250. About 100 ampicillin resistant colonies are obtained. 24 colonies are grown up and plasmid DNA is isolated from the cultures. Approximately 1 µg of plasmid DNA from each culture is digested with HindIII and the length of the digested DNA fragments analysed on a 1% agarose gel, using Hind III digested lambda DNA (Pharmacia, Sweden) as a size marker. The digested plasmid DNA of several colonies give DNA fragments with 1.0 kb and 3.3 kb of length. These plasmids are named pGEM TM -1/CL2 (see FIG. 3). They contain the amino terminus of the IgE-receptor proximal to the T7 polymerase promoter on the pGEM TM -1 vector DNA.

EXAMPLE 18

Transcription of the IgE-Receptor Related cDNA

10 µg of the plasmid pGEM TM -1/CL2 of Example 17 are digested with the restriction enzyme RsaI (Boehringer, Mannheim). 5 µl of 0.5M EDTA are added and the mixture is extracted once with phenol/chloroform (1:1, V:V) and once with chloroform. The DNA is concentrated by ethanol precipitation and dissolved in 20 µl TE buffer. 4 µl of the DNA solution are added to 100 µl of a solution containing 40 mM Tris-HCl pH 7.5, 6 mM MgCl2, 2 mM spermidine, 10 mM NaCl, 10 mM DTT, 1 unit/µl RNasin, 0.5 mM dNTP and 20 units of Riboprobe T7 RNA polymerase (Promega Biotec). The mixture is incubated for 1 hour at 37° C. Following the RNA synthesis reaction, two units of RQI TM DNAse (Promega Biotec) is added and the incubation at 37° C. continued for 1 h. The mixture is extracted once with phenol/chloroform and once with chloroform and the newly synthesized RNA recovered by ethanol precipitation. The RNA pellet is washed with 70% ethanol and finally dissolved in 20 µl H2O.

EXAMPLE 19

Translation of the Plasmid-Derived IgE-Receptor mRNA in Frog Oocytes and Detection of IgE-Receptor Protein The mRNA obtained in Example 18 is used directly for injection into frog oocytes as described in Example 3. The synthesis of IgE-receptor protein is tested in a RIA as described in Example 7. PolyA-mRNA from Example 1 is used as control sample. The results are compiled in the following table:

| Type of mRNA injected into the frog oocytes | 135I-Mab-135 bound in the RIA (input 3 × 10$^5$ cpm) |
| --- | --- |
| plasmid-derived mRNA (Example 18) | 15% |
| polyA-mRNA (Example 1) | 1.5% |
| no RNA | 0.1% |

EXAMPLE 20

Assembly of Plasmid pFK-1 and pFK-2 for the Expression in E. coli of a Polypeptide with IgE-Binding Factor Activity In this Example, plasmids are constructed which allow the production and secretion of polypeptides related to IgE binding factor in E. coli, whereby the amino terminal region from positions Met$_1$ to Ala$_{118}$ or Glu$_{133}$ which include the membrane anchor are deleted. 10 µg of pCL-2 plasmid-DNA is digested with the restriction enzymes HincII and RsaI. Fragments of 1.6, 1.25, 0.72, 0.46 and 0.23 kB are obtained and separated by electrophoresis through a 1% agarose gel in TBE buffer. The 1.25 kB DNA fragment is recovered as described in Example 13. In parallel, 10 µg of the plasmid pGEM TM -1 are linearized with 20 units HincII (Boehringer) in 50 µl of 10 mM Tris-HCl pH 7.6, 50 mM NaCl, 10 mM MgCl2 and 5 mM DTT. After 2 hours at 37° C., the reaction mixture is supplemented with 50 µl 1M Tris-HCl pH 8.5, 10 µl H2O and 20 units alkaline phosphatase from calf intestine (Boehringer) and the incubation is continued for 30 min at 37° C. The mixture is extracted three times with phenol-chloroform and then electrophoresed through a 1% agarose gel in TBE buffer. The plasmid DNA is recovered from the gel by electroelution as described in Example 13. 10 ng of the 1.25 kb cDNA fragment and 10 ng of the HincII cleaved pGEM ™-1 are ligated in a volume of 10 μl for 10 hours at 15° C. The reaction mixture contains in addition 10 mM Tris-HCl pH 7.5, 10 mM MgCl$_2$, 2 mM DTT, 0.5 mM ATP and 100 units T$_4$-ligase (Boehringer). 5 μl of the mixture are used to transform competent *E. coli* HB101 cells as described by Maniatis et al. (1), p. 250. The bacteria are plated on agar plates supplemented with 100 μg/ml ampicillin. About 50 ampicillin resistant colonies are obtained. 24 colonies are grown up and the plasmid DNA is isolated from each culture. Approximately 1 μg of plasmid DNA from each culture is digested with HindIII and the length from the digested DNA fragments analysed on a 1% agarose gel, using HindIII digested lambda DNA (Pharmacia, Sweden) as a size marker. The digested plasmid DNA of several colonies give DNA fragments with 0.5 kb and 3.6 kb, several others with 0.7 kb and 3.4 kb of length, corresponding to the two possible orientations of the fragment insertions. These plasmids are named pCAL-3 and pCAL-4 respectively (FIG. 4). One pCAL-3 clone and one pCAL-4 clone are grown up and the plasmid DNAs are isolated using the alkaline lysis method as described by Maniatis et al. (1), p. 90. 10 μg of the pCAL-4 plasmid DNA is digested with HindIII and 10 μg of pCAL-3 plasmid DNA is digested with BglII and BamHI restriction enzyme. The fragments are separated by electrophoresis and the 0.8 BglII to BamHI and 0.75 kb HindIII to HindIII fragments are recovered by electroelution as described in Example 13. In parallel, 10 μg of pIN-III-ompA-2 plasmid DNA (Gharayeb et al. (5)) and 10 μg of pIN-III-ompA-3 plasmid DNA are digested with HindIII and BamHI, respectively. These two plasmids are well known secretion cloning vectors in *E. coli* which allow the cloning of foreign DNA fragments in two reading frames fused to sequences coding for the signal peptide of the OmpA protein. Next, the linearized plasmids are treated with alkaline phosphatase from calf intestine and the linear DNA is purified on a 0.8% agarose gel as described above. Two ligation mixtures are set up containing in a volume of 20 μl, 10 ng of HindIII cleaved pIN-III-ompA-2 and 10 ng of 0.8 kb HindIII to HindIII fragment (mix 1), and 10 ng of 0.75 kb BglII to BamHI fragment together with 10 ng of BamHI-cleaved pIN-III-ompA-3 (mix 2). The reaction mixtures contain in addition 10 mM Tris-HCl pH 7.5, 10 mM MgCl$_2$, 2 mM DTT, 0.1 mM ATP and 100 units T$_4$ ligase (Boehringer Mannheim). After 12 hours at 15° C., 5 μl of the mixtures are used to transform competent *E.coli* HB101 cells as described by Maniatis et al. (1), p. 250. 50 to 100 ampicillin resistant colonies are obtained from mix 1 and mix 2. 12 colonies from each mix are grown up and the plasmid DNA is isolated from the cultures. Approximately 1 μg of the plasmid DNA from each culture is digested with PstI and EcoRI (mix 1) and with BamHI and EcoRI (mix 2). The length of the DNA fragments is analysed on a 1% agarose gel using HindIII digested lambda DNA (Pharmacia, Sweden) as a size marker. Several plasmids derived from mix 1 produce a 0.75 kb fragment. These plasmids are named pFK-2. They contain the DNA coding for amino acids Ala$_{134}$ to Ser$_{321}$ of the IgE-receptor fused to the OmpA signal sequence. In analogy several plasmids derived from mix 2 produce a 0.8 kB fragment. These plasmids are named pFK-1. They contain the DNA coding for amino acids Asp$_{119}$ to Ser$_{321}$ fused to the OmpA signal sequence.

EXAMPLE 21

Detection of IgE-Binding Factor Related Polypeptide in *E. coli* Strains Carrying Plasmids pFK-1 and pFK-2

10 ng of plasmid pFK-1, pFK-2 and plasmid pIN-III-ompA-2 as control are used to transfect competent *E. coli* BZ 234 and *E. coli* B1472 cells. Competent cells are made and transfected as described by Maniatis et al. (1), p. 250. Over 100 ampicillin resistant colonies are obtained from each transfection. One colony is transferred into 2 ml of LB-broth supplemented with 100 μg ampicillin/ml and grown at 37° C. overnight. 1 ml of the cultures is transferred into 100 ml LB-broth supplemented with 100 μg ampicillin/ml. The cells are grown with vigorous shaking (250 rpm) at 37° C. 10 ml aliquots are removed after 4, 7, 10 and 24 hours. The aliquots are processed immediately. The cells are collected by centrifugation with 1000 g at room temperature for 10 minutes. The supernatant is discarded and the cells are suspended in 2.5 ml of 20% sucrose, 0.1M Tris-HCl pH 8.0.

The mixtures are left at room temperature for 20 minutes and the cells are collected again by centrifugation. The supernatants are discarded and the cells suspended in 1.5 ml of ice-cold H$_2$O. The mixtures are incubated on ice for 20 minutes and centrifuged at 4° C. with 12000 g for 10 minutes. 5 μl of the supernatants are added to 100 μl of HBSS-FCS and these samples are analysed with the RIA described in Example 7. pIN-III-ompA-2 is used for control. The following results are obtained:

| culturing time | BZ 234 + pFK-1 | BZ 234 + pFK-2 | BZ 234 + pIN-III-ompA-2 | B 1472 + pFK-1 | B 1472 + pFK-2 | B 1472 + pIN-III-ompA-2 |
|---|---|---|---|---|---|---|
| 4 h | 4355 | 3516 | — | 3432 | 2255 | 50 |
| 7 h | 6869 | 5066 | 120 | 4853 | 2754 | 0 |
| 10 h | 8396 | 5706 | — | 6084 | 5281 | 0 |
| 24 h | 7890 | 5206 | 89 | 5595 | 5088 | 76 |

Values are given as cpm measured per well in the RIA as described in Example 7. The input of radioactivity per well is 325 000 cpm.

EXAMPLE 22

Preparation of an Immunoaffinity Gel for the Purification of the IgE Binding Factor Protein Affi-Gel ®10 material (Bio-Rad) is washed as directed by the manufacturer with cold distilled water and coupling buffer pH 8.0 (0.1M NaHCO$_3$ solution). A 50% strength suspension of gel in 2 ml coupling buffer is introduced into a plastic tube and mixed with the same volume of a solution that contains 10 mg of Mab-135 or Mab-176, and the mixture is rotated for 4 hours at room temperature. The gel is again washed with coupling buffer. In order to block the active sites that are still free, the gel is treated for 2 hours at room temperature with 0.1 ml of 1M ethanolamine-HCl, pH 8.0, then washed with PBS containing 10 mM of sodium azide and kept therein at 4° C.

EXAMPLE 23

Fermentation of Transformed Cells and Isolation of IgE Binding Factor Protein from the Bacterial Culture One colony of *E. coli* BZ 234 containing the plasmid pFK-1 from Example 20 is transferred into 10 ml of LB-broth medium supplemented with ampicillin (100 μg/ml) and grown at 37° C. and vigorous shaking overnight. 1 ml aliquots of the culture are transferred into 6 flasks, each containing 800 ml LB-broth supplemented with ampicillin (100 μg/ml). The cells are grown up under vigorous shaking (250 rpm) at 37° C. for 8 hours and collected by centrifugation with 1000 g at room temperature for 10 minutes. The supernatant is discarded and the cells are suspended in 300 ml of a solution containing 20% sucrose, 30 mM Tris-HCl pH 8.0 and 1 mM EDTA. The suspension is left at room temperature for 20 minutes and the cells are collected again by centrifugation. The supernatant is discarded and the cells suspended in 200 ml of ice cold $H_2O$. The suspension is incubated on ice for 20 minutes and centrifuged at 4° C. with 10000 g for 15 minutes in a rotor of a Sorvall centrifuge. The supernatant (about 180 ml) is carefully recovered, supplemented with sodium azide (0.1 mg/ml) and filtered through a Nalgene ® sterilization filter unit (0.2 micron; Nalge Company, Rochester, N.Y., U.S.A.). The filtered solution is loaded onto a 2 ml column of Mab-135 or Mab-176 coupled Affi-Gel ®10, obtained as described in Example 22, at a flow rate of 50 ml/hour. The gel is washed successively with 20 volumes PBS supplemented with 0.5 NaCl and 0.05% Tween ®20, 5 volumes PBS and 5 volumes NaCl 0.9%. The protein content of the wash solutions is screened by measuring the absorbance at 280 nm to ensure complete removal of unbound proteins. The column is then eluated with aliquots of 1 ml volume each containing 0.1M glycine-HCl, 0.1M NaCl, pH 2.6. The fractions containing proteins are pooled, and neutralized with 1M Tris.

The concentrated solutions of a purified polypeptide of the invention are obtained by treatment with an ISCO electrophoretic concentrator Model 1750 (Isco Inc.) and a Spectrapor ® membrane (Spectrum Medical Industries) with 3.5 KD cut-off. The solutions are dialyzed against 25 mM ammonium acetate, pH 8.3 and thereby concentrated to a volume of 0.2 ml.

The purified protein is analyzed in the following way: Fractions are incubated with Laemmli buffer then separated into individual proteins by 12% SDS-PAGE and silver staining as described in the BioRad manual. Proteins with a approximate molecular weight of 25 KD are detected. They are transferred electrophoretically for 4 hours at 0.12 ampere with transfer buffer to a nitrocellulose membrane. The membrane is blocked with Tris-buffered saline containing 10% FCS. Strips are cut and reacted individually with Mab-135 and Mab-176, each at 10 μg/ml. After 6 hours incubation, the strips are washed and reacted overnight with horseradish peroxidase goat anti-mouse IgG. The strips are washed and developed with 4-chloro-1-naphthol (peroxidase substrate) as detailed in the BioRad instruction manual. The Mab-135 and Mab-176 monoclonal antibodies each react with the 25 KD protein fragment.

EXAMPLE 24

Expression of Polypeptide with IgE-Binding Factor Activity in *E. coli* Under the Control of the Promoter $P_L$ of Phage λ

24.1 Construction of Expression Plasmid

Plasmid pHRi148 (European Patent Application EP 146 785) is used as an intermediate vector. 10 μg of pHRi148 plasmid DNA are digested with NcoI, then treated with Klenow polymerase and dNTP (50 μM) in order to render the ends blunt-ended. The DNA is further digested with BamHI and treated with alkaline phosphatase. The 4.3 kb vector DNA is isolated by agarose gel electrophoresis. In parallel, 10 μg of pCAL3 plasmid DNA (Example 20) are cleaved with BglII, then treated with Klenow polymerase and dNTP (50 μM). The DNA is further cleaved with BamHI and the 0.78 kb insert DNA fragment isolated by agarose gel electrophoresis. 10 ng of purified vector and 3 ng of purified insert DNA are ligated and the mixture used to transform competent *E. coli* HB101 cells. A clone with the correct recombinant plasmid is selected on the basis of restriction enzyme analyses (FIG. 5).

10 μg of DNA of a correct plasmid is digested with BamHI and EcoRI. The 0.79 kb insert DNA is isolated by agarose gel electrophoresis. In parallel, 10 μg of pPLc24 plasmid DNA [Remaut, E. et al. (1981), GENE 15, 81-93] is digested with EcoRI and BamHI, then treated with alkaline phosphatase and the 2.9 kb vector DNA is purified by agarose gel electrophoresis. 10 ng of the 2.9 kb vector DNA and 3 ng of the 0.79 kb insert DNA are ligated and then used to transform competent *E. coli* K12 cells. Standard restriction analysis is performed to select a correct plasmid (pPL-BF; FIG. 5). This plasmid carries the DNA sequence of the formula II coding for amino acids 119 to 321 of the polypeptide of formula I downstream of the heat inducible $P_L$ promoter. Amino acid 119 is preceded by a methionine which has been added during the intermediate cloning step in plasmid pHRi148.

Plasmid pPL-BF is used to transform *E. coli* strains W3110 and HB101, both harbouring λcI857 (Remaut et al., loc. cit.). The transformants are plated out on LB-plates containing 40 μg/ml of kanamycin and ampicillin and grown by incubation at 30° C. for 24 hours. Resulting recombinant colonies are used for fermentation.

24.2 Fermentation

Recombinant *E. coli* strains obtained in Example 24.1 are grown at 30° C. overnight in LB-broth containing 40 μg/ml of ampicillin and kanamycin. The cultures are diluted 1:5 with the same medium and incubated at 42° C. for 4 hours. The cells are collected by centrifugation.

24.3 Purification of Polypeptides with IgE-Binding Activity 22.5 ml of a cell suspension ($OD_{650}=20$) in 50 mM Hepes pH 8.0, 30 mM NaCl and 0.1% ethanolamine, prepared from a bacterial pellet of Example 24.2, are mixed with 18 g of urea. The suspension is sonified 3×30 sec with 30 sec intervalls with a MSE Soniprep ® 150 using a 9.5 mm probe and 24 micron amplitude. The lysate is cleared by centrifugation at 17000 rpm in a Sorvall SS34 rotor for 30 min at 20° C. The supernatant is dialysed at 4° C. against three changes of 10 mM Hepes pH 7.5 and 130 mM NaCl. The dialysate is cleared by centrifugation for 30 min at 17000 rpm in a SS34 rotor (Sorvall) at 4° C., and the supernatant supplemented with sodium azide (0.1 mg/ml). The polypeptides with IgE-binding activity are further purified and analysed as described hereinbefore, e.g. in Example 22 and 23.

EXAMPLE 25

Expression of a Polypeptide with IgE-Binding Factor Activity in Yeast Saccharomyces Cerevisiae

25.1 Construction of Expression Plasmid pJDB207R/PHO5-BF (FIG. 6)

To prepare the vector DNA, 10 μg of plasmid DNA pJDB207R/PHO5-TPA(12-2) (European Patent Application EP 143081) are digested to completion with BamHI. The digested DNA is treated with alkaline phosphatase. The large 6.85 kb BamHI fragment is separated from the small fragment on a 1% agarose gel in TBE buffer and the 6.85 kb DNA fragment is recovered from the gel by electroelution. A DNA fragment encoding the inducible PHO5 promoter and the PHO5 signal sequence is derived from plasmid pJDB207/PHO5-TPA18 (European Patent Application 143'081). 50 μg of this plasmid is digested to completion with BamHI and HindIII and the 2.3 kb fragment is isolated. 5 μg of this fragment are further digested with BalI and the 0.58 kb fragment is isolated. 20 ng of the vector DNA described above, 4 ng of the 0.58 kb fragment, 8 ng of the 0.8 kb BglII/BamHI cDNA fragment derived from pCAL3 (Example 20) and 0.1 ng of a chemically synthesized ds DNA linker with the nucleic acid sequence: 5'pCCAATGCA-3'/3'-GGTTACGT-CTAGp-5' are mixed and ligated for 24 hours and 15° C. in a volume of 20 μl. The ligated DNA is used to transform competent E. coli HB101 cells. The plasmid DNA of about 100 ampicillin-resistant colonies is analysed by restriction enzyme digestion. A few colonies are found which have taken up all three insert DNA fragments in the desired orientation (plasmid pJDB207R/PHO5-BF; FIG. 6). The correct structure of the construction at the junctions between the PHO5 signal sequence, the chemically synthesized linker DNA and the IgE-BF cDNA are verified by sequencing.

25.2 Transformation and Fermentation of Yeast

Plasmid pJDB207R/PHO5-BF is transformed into Saccharomyces cerevisiae strain GRF18 (α, his 3-11, his 3-15, leu 2-3, leu 2-112, kan ®) using the transformation protocol described by Hinnen et al. (Proc. Natl. Acad. Sci. USA 1978, 75, 1979). Transformed yeast cells are selected on yeast minimal media plates deficient in leucine. Single transformed yeast colonies are isolated and referred to as Saccharomyces cerevisiae GRF18 [pJDB207R/PHO5-BF]. Such transformed yeast cells are grown in 50 ml of yeast minimal medium (Difco Yeast Nitrogen Base) without amino acids to which 2% glucose, 20 mg/l L-histidine and 10 g/l L-asparagine are added with shaking at 30° C. for 25 hours to a density of $3 \times 10^7$ cells/ml. The cells are washed in 0.9% NaCl and used to inoculated 100 ml of low $P_i$ minimal medium prepared according to the recipe of the Difco Yeast Nitrogen Base medium (without amino acids) with 0.03 g/l KH$_2$PO$_4$, 1 g/l KCl, 10 g/l L-asparagine instead of (NH$_4$)$_2$SO$_4$, 2% and 1 g/l L-histidine. The medium is inoculated to a starting OD$_{600}$ of 0.25. The cells are grown at 30° C. for up to 48 hours and harvested at an OD$_{600}$ of about 10.

Cells of 35 ml of low $P_i$ medium are collected by centrifugation and resuspended in a total volume of 4 ml of cold 66 mM sodium phosphate buffer pH 7.4 and 0.1% (v/v) Triton X-100 ®. The cell suspension is transferred to a 30 ml Corex tube. 8 g of glass beads (0.4 mm in diameter) are added and the suspension is shaken on a Vortex Mixer (Scientific Instruments Inc., U.S.A.) at full speed for 4 min and then cooled in an ice bath. More than 90% of the cells are broken by this procedure. Cell debris and glass beads are sedimented by centrifugation for 10 min at 8000 rpm at 4° C. in a Sorval HB4 rotor. Polypeptides with IgE-binding factor activity are purified from the supernatants using affinity chromatography as described in Examples 22 and 23.

EXAMPLE 26

Assembly of Plasmids pCAL5-R/ND and pCAL8-BF/ND for the Expression of Polypeptides with IgE-Binding Activity in Cultured Mammalian Cells.

In this example, the construction of plasmids pCAL5-R/ND and pCAL8-BF/ND is described (see FIG. 7). They allow the production of membrane-bound IgE receptor or secreted IgE-binding factor in cultured mammalian cells. Furthermore, these plasmids are designed for the selection of gene amplification in the host cells, a process leading to high yields of the desired polypeptide.

26.1 Construction of Plasmid pCAL5

Plasmid pSV2911neo [Asselbergs, F. A. M., et al. (1986) J. Mol. Biol. 189, 401–411] is used to prepare the vector DNA. It is digested with the restriction enzymes HindIII and SalI. Fragments of 3.9 and 1.8 kb are obtained. The mixture is treated with alkaline phosphatase and the 3.9 kb fragment is isolated after electrophoresis through a 1% agarose gel.

In parallel, two DNA inserts are prepared which code for the IgE receptor and the 3'-half of the rabbit beta-globin gene, respectively. On the one hand, 10 μg of plasmid pCAL3 (Example 20; FIG. 4) are digested partially with HindIII and completely digested with BamHI. The cDNA insert of 1.26 kb is isolated by agarose gel electrophoresis and gel elution. On the other hand, 10 μg of plasmid pUβ [Weber, F. and Schaffner, W. (1985) Nature 135, 75–77] are digested to completion with BamHI and SalI. The 1.2 kb DNA fragment is isolated. It contains the large intron and the poly(A) signal of the rabbit beta-globin gene.

10 ng of the vector DNA from above and 10 ng of each insert DNA are ligated. The resulting DNA is used to transfect competent E. coli HB101. A recombinant plasmid (pCAL5; FIG. 7) is selected which shows the expected restriction pattern as expected after the uptake of both DNA inserts into the vector DNA.

26.2 Construction of Plasmid pCAL5-R/ND 10 ng of pCAL5 plasmid DNA are partially digested with SalI. DNA molecules which are cut only once, and thus represent full-length linears, are purified by agarose gel electrophoresis. In parallel, 10 μg of pND2 plasmid DNA (Asselbergs et al.; loc. cit.) are cleaved to completion with XhoI and SalI.

This plasmid contains two selection markers, neomycin (neo) and dihydrofolate reductase (dhfr), which allow to select for integration and amplification, respectively, of foreign DNA in the genome of mammalian hosts. The cleaved pND2 DNA is treated with alkaline phosphatase. Then, 10 ng of SalI-cleaved pCAL5 and 10 ng of SalI/XhoI-cleaved pND2 plasmid DNA are mixed and ligated. The resulting DNA is used to transform competent E. coli HB101 cells. The transformed cells are spread onto a agar plate containing LB-broth and 50 μg/ml kanamycin. A recombinant plasmid (pCAL5-R/ND, FIG. 7) displaying the expected DNA restricted pattern is chosen for the expression of the IgE receptor in mammalian hosts. It contains the neo- and dhfr-selection markers downstream of the IgE-receptor cDNA. The direction of transcription is identical for all three genes.

26.3 Construction of Plasmid pCAL8-BF/ND

The plasmid pCAL8-BF/ND is a derivative of the plasmid pCAL5-R/ND described above, wherein the DNA sequence coding for amino acids 1 to 147 of the polypeptide of formula I are replaced by a new DNA sequence coding for the signal sequence of the avian influenza hemagglutinin. This change allows the secretion of IgE-binding factors comprising amino acids 148 to 321 of the polypeptide of formula I.

To this end, a ds DNA fragment is chemically synthesized according to standard methods described in references 4, 5, 6, 6a, 7, 8, having the formula:

5'-pAGCTTACCATGGCTACCCAGATCTTGGTGTTCGCTCTGGTGGCCGTCATTCCTACAAACGCGC

ATGGTACCGATGGGTCTAGAACCACAAGCGAGACCACCGGCAGTAAGGATGTTTGCGCGATTP-5'

0.2 ng of this DNA is ligated with 10 ng of vector DNA and 2 ng of a 0.7 kb DdeI/XbaI cDNA insert. The vector is obtained from pCAL5 plasmid DNA by (a) digestion to completion with XbaI nd HindIII, (b) dephosphorylation with alkaline phosphatase, and (c) agarose gel purification of the 5.9 kb vector DNA. The 0.7 kb cDNA insert fragment is derived from pCAL3 (Example 20). 30 μg of pCAL3 plasmid DNA are digested with HindIII and XbaI, and the 0.8 kb cDNA insert is isolated by agarose gel purification. 3 μg of this 0.8 kb fragment are digested with DdeI, thereby producing DNA fragments of 0.1 and 0.7 kb. Finally the 0.7 kb DNA fragment is isolated by agarose gel electrophoresis and purification.

The ligated DNA is used to transform competent *E. coli* HB101 cells. A recombinant plasmid (pCAL8; FIG. 7) is selected which shows the expected restriction fragments, as expected after the integration of the DNA insert into the vector DNA.

10 μg of pCAL8 plasmid DNA are digested to completion with SalI. The linear DNA molecules are purified by agarose gel electrophoresis. 10 ng of SalI cleaved pCAL8 are ligated with 10 ng SalI/XhoI-cleaved pND2 plasmid (Example 26.2). The ligated DNA is used to transform competent *E. coli* HB101 cells which are plated on a agar plate containing LB-medium supplemented with 50 μg/ml kanamycin. A recombinant plasmid (pCAL8-BF/ND; FIG. 7) is selected for the expression and production of IgE-BFs in transformed mammalian hosts.

EXAMPLE 27

Selection of Transformed Mammalian Cell Lines Expressing Polypeptides with IgE-Binding Activity The methods used for transfection of DNA into mammalian cells, as well as selection of transformed cells and selection for gene amplification have been described in detail [U.S. Pat. No. 4,399,216 (1983); Kaufman, R. J. and Sharp, P. A. (1982), J. Mol. Biol. 159, 601-621] and are well known to the ones experienced in the art. A dihydrofolate reductase negative mutant (dhfr−) of a Chinese hamster ovary cell line is used as host [Cell line DUKX-B1; Chasin, L. A. and Urlaub, G., (1980) Proc. Nat. Acad. Sci. USA 77, 4216-4220]. The cells are maintained in MEM medium (Gibco, Paislay, Scotland) supplemented with 5% dialysed FCS and 0.1 mg/ml gentamycin (Gibco). Subconfluent CHO cells are transfected with 10 μg pCAL5-R/ND or pCAL8-BF/ND plasmid DNA using the Ca-phosphate co-precipitation method. The transfected cells are grown in Alpha-MEM medium supplemented with 5% FCS, gentamycin and 0.5 mg/ml G418 (Gibco).

After two weeks, single colonies of G418-resistant cells grow out. 48 colonies are transferred individually into the wells of a 24-well microtiter plate and grown to confluency in the selection medium described above. Then, aliquots of the medium are removed and tested for the presence of IgE-binding activity using the RIA described in Example 7. About 50% of the colonies are positive and produce approximately 0.1-10 ng of recombinant polypeptide per ml. The transformed colonies derived from plasmid pCAL8-BF/ND are generally higher producers than the ones obtained with plasmid pCAL5-R/ND. The five best producing colonies are used for gene amplification with methotrexate (Kaufman and Sharp op. cit.). After several rounds of amplification, cell lines are obtained which produce up to 1 μg/ml of recombinant polypeptide. The best producer, cell line CHO-BF/ND, is grown into bulk cultures. Approximately $3\times10^6$ cells are seeded per tissue culture flask (Falcon, 175 $cm^2$) with 50 ml of selection medium. After the cell layer has reached confluency, the medium is removed and replaced with 50 ml of Alpha-MEM medium supplemented with 1% FCS and 0.1 mg/ml gentamycin. The medium is collected twice per week for several weeks. It is centrifuged for 10 min at 5000 g and stored at −20° C. Finally, recombinant polypeptides with IgE-binding activity are purified from the combined supernatants by affinity chromatography as described hereinbefore, e.g. in Examples 22 and 23.

Purification of Natural IgE-BF from RPMI 8866 Cells and Sequence Analysis

By purification of IgE-BF containing fractions of RPMI 8866 cell supernatants (EP 86810244.3) according to the following Examples B to D it is possible to obtain an IgE-BF which is pure enough for sequencing and determination of the amino terminal.

EXAMPLE A

Enzyme-Linked-Immuno-Sorbent-Assay (ELISA) of IgE-BF

The fractions are assayed for IgE-BF in the following way: PVC microtiter plate wells are coated with Mab-176 (5 μg/ml in PBS; 100 μg per well) overnight in a humidity chamber at room temperature. The plates are washed twice with PBS before nonspecific binding sites are blocked with PBS containing 0.2% gelatine (150 μl/well; 1 h at 37° C.). Plates are washed again twice with PBS. Fractions from chromatography experiments are diluted 1/50 in PBS, added to the wells (100 μl/well) and incubated overnight at room temperature in a humidity chamber. Plates are washed 4 times with PBS. Bound IgE-BF is detected by adding Mab-135 to which biotin had been attached covalently (Example 19, EP 86810244.3) (0.5 μg/ml in PBS containing 0.2% gelatine; 100 μl/well) and incubated 4 h at 37° C. in a humidity chamber. After washing with PBS (4 times) the plates are incubated with 100 μl of a conjugate of avidin and alkaline phosphatase (Sigma Cat. No. A 2527 0.5 μg/ml) in PBS containing 0.2% gelatine for 2 h at 37° C. After additional washing with PBS the plates are developed with 1 mg/ml p-nitrophenyl phosphate disodium in substrate buffer (100 mg $MgCl_2 \times 6\ H_2O$, 200 mg $NaN_3$, 97 ml diethanolamin dissolved in 800 ml $H_2O$, pH adjusted to 9.8 with 37% HCl). The yellow colour reaction is optimal after 20–40 min at 37° C. The reaction is then stopped with 50 μl NaOH (1M) per well. The optical density is determined using a Model 2550 EIA Reader (Bio-Rad) at 405 mm.

EXAMPLE B

Purification of IgE-BF from Human B-Cell Supernatants by Immunoaffinity Chromatography 10 liter culture supernatant from RPMI 8866 cells are filtered through a 20 ml column of Mab-45-affigel (Example 10 of EP 86810244.3) at a flow rate of 120 ml/h. The gel is washed with PBS. The protein content of the flow-through is monitored by on-line absorbance at 280 nm by means of a Uvicord® spectrophotometer to ensure complete removal of unbound proteins. The column is eluted with 50 ml 0.1M glycine-HCl, pH 2.6. Fractions are collected in tubes containing an equal amount of 1M Tris-HCl, pH 8.0 and 0.5% Tween 20. IgE-BF containing fractions are pooled and dialyzed against 10 mM Tris-HCl, pH 7.4.

EXAMPLE C

Purification of IgE-BF by Ion Exchange Chromatography

Purified IgE-BF of Example B is loaded on a SynChropak AX 300 anion exchanger column (SynChrom Inc., Linden, IN). The column is washed with 10 mM Tris-HCl, pH 7.4, and the protein is eluted with a gradient of 0 to 1M NaCl in 100 min at a flow-rate of 1 ml/min. Elution is monitored for UV absorbance at 254 nm. The fractions are collected into 1% octylpyranoglucoside (Sigma) and assayed for IgE-BF as described in Example A.

EXAMPLE D

Further Purification of IgE-BF by Reverse Phase Chromatography 50 ml of IgE-BF of Example C is dialyzed against 0.5 l PBS and twice against 0.5 l PBS containing 0.1% octylpyranoglucoside. After lyophylization the IgE-BF is solubilized in 1.5 ml $H_2O$ and again dialyzed against $2 \times 0.5$ l PBS containing 0.1% octylpyranoglucoside. Reversed phase chromatography is performed on a SynChropak RP-4 (SynChrom) column in 0.1% TFA (Pierce) and 5% acetonitrile (Merck). Elution of IgE-BF is obtained by applying a gradient of 5–60% acetonitrile in 0.1% TFA during 30 min at a flow-rate of 0.5 ml/min. Elution is monitored for UV absorbance at 254 nm. 1 ml fractions are collected into 0.05% SDS and assayed for IgE-BF as described in Example A. The purity of IgE-BF is controlled by SDS-PAGE with subsequent silver staining (EP 86810244.3 Example 22).

EXAMPLE E

Amino Acid Sequence Analysis of IgE-BF

The purified IgE-BF of Example D is subjected to N-terminal amino acid sequence analysis using a positive phase protein sequencer model 470 (Applied Biosystems) according to the method of M. W. Hunkapillar and L. E. Hood, Methods in Enzymology 91, 399, 1983. The amino-thiozolinone derivatives are rearranged to phenylthiohydantoin (PTH) amino acids by treatment with 25% aqueous TFA at 50° C. The PTH amino acids are analyzed on a Zorbax CN® HPLC column (Du Pont, $200 \times 4.6$ mm) (R. Knecht et al., Anal. Biochem. 130, 65, 1983). The following N-terminal amino acid sequence is found for 40% of the material:

```
148 149         155         160         163
  L  X  M E L Q  V  X S G F  V  X N T  X  P
```

$X_{149}$, $X_{155}$, $X_{160}$ and $X_{163}$ represent non-determined amino acids. This sequence is in accordance with the sequence of the IgE-receptor determined by cDNA analysis, starting at amino acid No. 148 of the receptor.

The following N-terminal amino acid sequence is found for 60% of the material:

```
150 151             160         163
  M  X L Q V S S G F  V  X N T  X  P E K
```

$X_{151}$, $X_{160}$ and $X_{163}$ represent non-determined amino acids. This sequence is in accordance with the sequence of the IgE receptor determined by cDNA analysis, starting at amino acid No. 150 of the receptor.

EXAMPLE 28

High Level Expression in *E. coli* of a Polypeptide with IgE-Binding Factor Activity

28.1 Construction of Expression Plasmid 10 ng of the purified 2.9 kb vector DNA of example 24.1 (plasmid pPLc24 cut with EcoRI and BamHI) are mixed with 0.1 ng of the oligonucleotide 5'-pAATTT-GGAGGAAAAAATTATG (Pharmacia, No. 27-4878-01) and 0.1 ng of the oligonucleotide 5'-pGATCCATAATTTTTTCCTCCA (Pharmacia, No. 27-4898-01) in 20 μl of a solution containing 10 mM Tris-HCl pH 7.5, 10 mM $MgCl_2$, 2 mM DDT, 0.1 mM ATP and 100 units $T_4$ DNA ligase (Boehringer, Mannheim). After 16 hours at 4° C., the mixture is used to transform competent *E. coli* K12 cells. Individual colonies are grown up and plasmid DNA is isolated thereof. Standard restriction analysis is performed to select a correct plasmid (pPL.PTIS; see FIG. 8) which is cut by BamHI but not by EcoRI. The correct insertion of the oligonucleotides is confirmed by DNA sequencing. The newly inserted DNA fragment codes for a portable translation initiation site (PTIS, Pharmacia). 10 μg of pPL.PTIS plasmid DNA is digested with BamHI, then treated with alkaline phosphatase and the linear 2.9 kb vector DNA is purified by agarose gel electrophoresis. 10 ng of this vector DNA is ligated with 3 ng of the 0.8 kb BglII to BamHI fragment derived from plasmid pCAL-3 (example 20) and then used to transform competent E. coli K12 cells. Plasmid DNA is isolated from individual colonies and standard restriction analysis is performed to select a plasmid, pPL.PTIS-BF, having the 0.8 kb insertion in the correct orientation (FIG. 8).

Plasmid pPL.PTIS-BF is used to transform E. coli strains W3110 and HB101, both harbouring λI857 (Remaut et al., loc. cit.). The transformants are plated out on LB-plates containing 40 μg/ml of kanamycin and ampicillin and grown by incubation at 30° C. for 24 hours. Resulting recombinant colonies are used for fermentation.

28.2 Fermentation

Recombinant E. coli strains obtained in Example 28.1 are grown as described in example 24.2. After 3 hours of induction at 42° C., the cultures are cooled for 30 minutes in an ice/water bath and collected by centrifugation.

28.3 Purification of Polypeptides with IgE-Binding Activity

The cell pellet obtained from 1 l of heat-induced culture is resuspended in 20 ml of 50 mM Tris-HCl pH 7.5., 1 mM EDTA at 4° C. The cell suspension is sonified while constantly cooled on ice (MSE Soniprep ® 150, 9.5 mm probe, 24 micron amplitude) for 4×30 seconds with one minute intervals. The suspension is then centrifuged for 10 minutes (Sorvall centrifuge, HB-4 rotor, 9000 rpm, 4° C.). The pellet is resuspended in 20 ml of 50 mM Tris-HCl pH 7.5, 1 mM EDTA at 4° C. and sonified for 30 seconds as described above. The suspension is centrifuged as described above and the washing cycle repeated twice more.

BRIEF DESCRIPTION OF THE FIGURES

FIG. 9: Amino acid sequence of the polypeptide of formula (I) in which the single letters represent the following naturally occurring L-amino acids: (A) alanine, (C) cysteine, (D) aspartic acid, (E) glutamic acid, (F) phenylalanine, (G) glycine, (H) histidine, (I) isoleucine, (K) lysine, (L) leucine, (M) methionine, (N) asparagine, (P) proline, (Q) glutamine, (R) arginine, (S) serine, (T) threonine, (V) valine, (W) tryptophan, (Y) tyrosine.

FIG. 10: DNA sequence (formula II) of the pCL-2 cDNA insert. The coding region for the polypeptide of formula (I) is marked by the amino acid symbols the meanings of which are given in the legend of FIG. 9. Restriction sites

Figure 1:
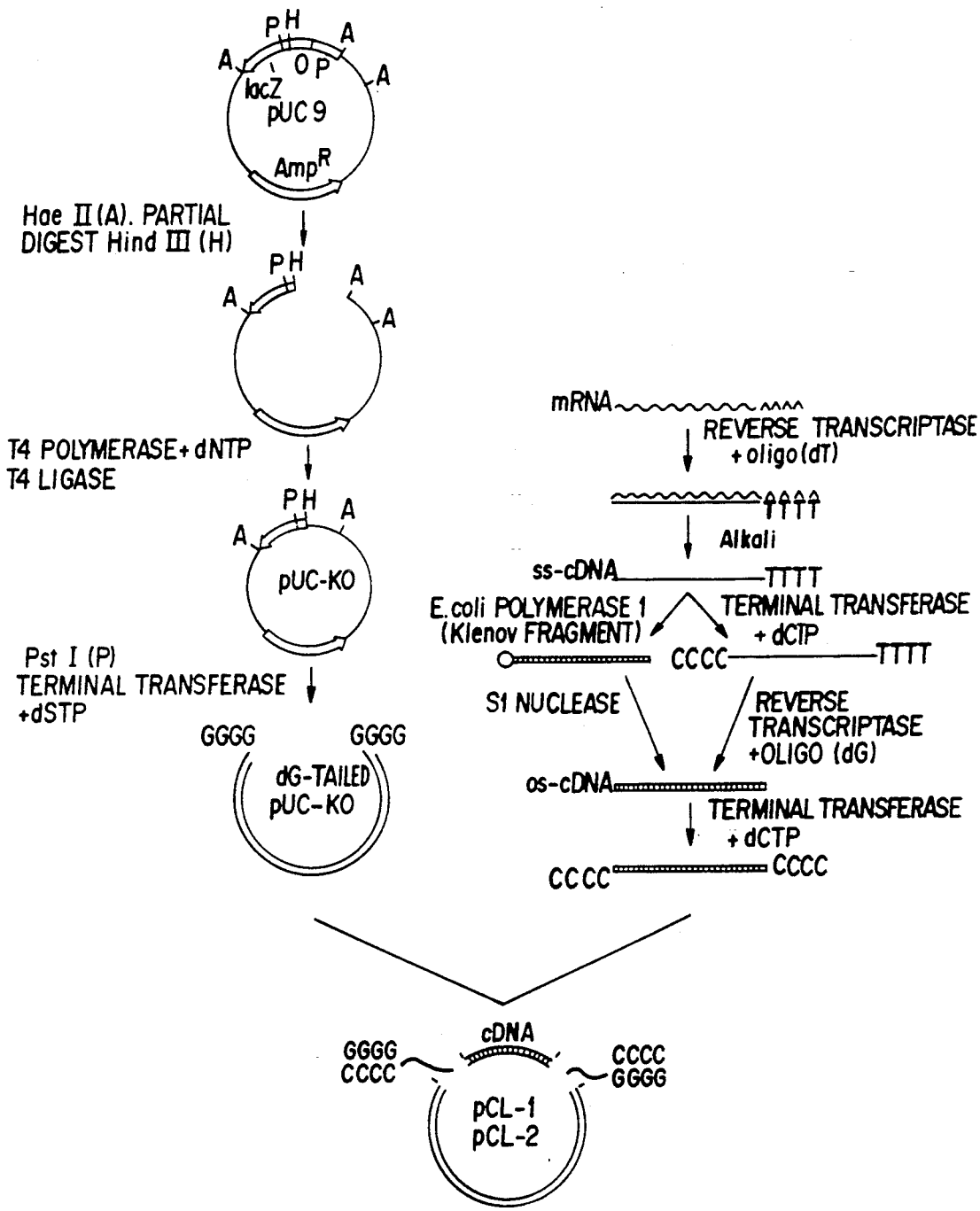
FIG. 1: Preparation of plasmids pCL-1 and pCL-2 containing as insert ds-cDNA from mRNA isolated from RPMI 8866 B-cells. The insert cDNA is coding for polypeptides related to IgE-receptors and IgE-binding factors.
Figure 2:
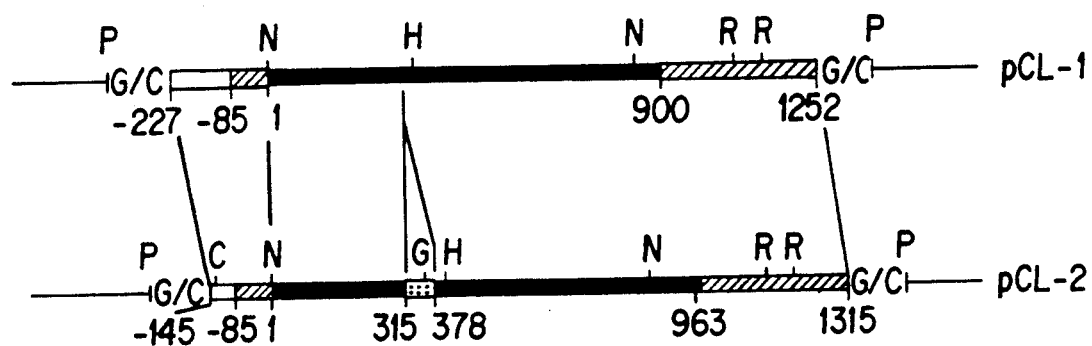
FIG. 2: The two inserts of the plasmids pCL-1 and pCL-2 are compared, showing the coding regions identical to both inserts, the non-coding regions identical to both inserts, coding region only present in pCL-2 and non-coding regions different in both inserts, as well as some restriction sides.
Figure 3:
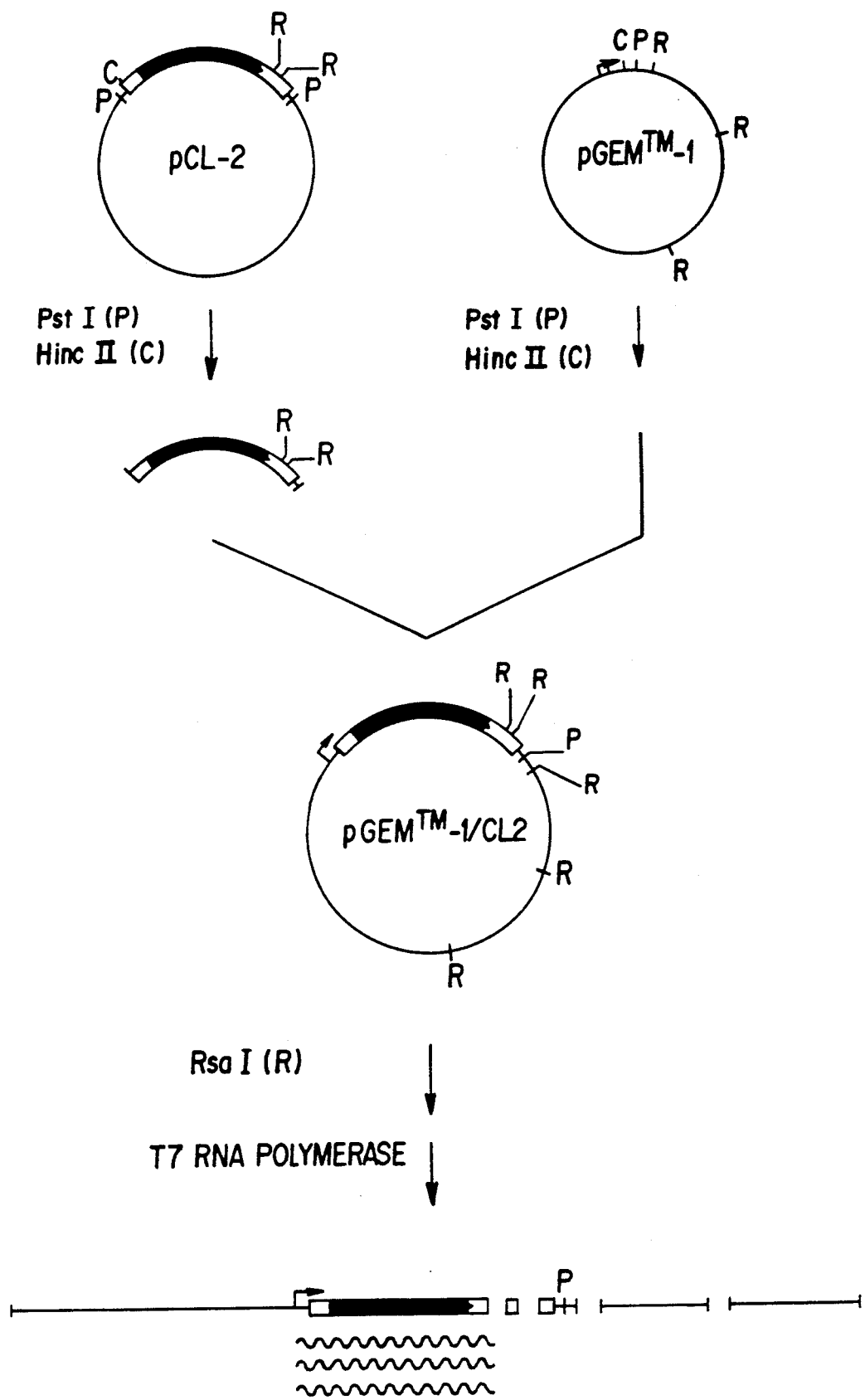
FIG. 3: Construction of the plasmid pGEM ™-1/CL2 from pCL-2 and pGEM ™-1, and transcription of the DNA insert into mRNA.
Figure 4:
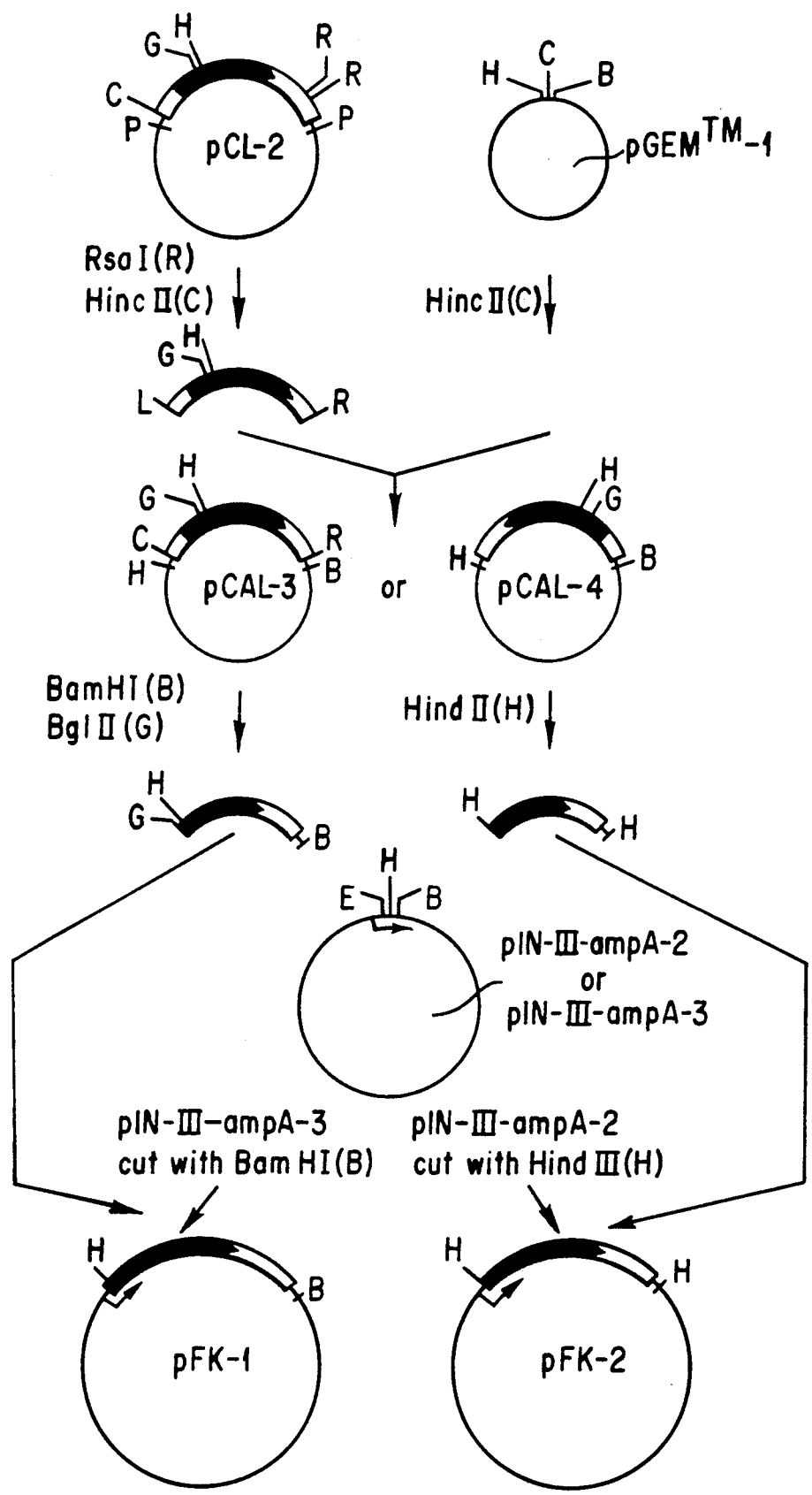
FIG. 4: The construction of the plasmids pFK-1, with the insert coding for amino acid sequence $Asp_{119}$ to $Ser_{321}$, and pFK-2, coding for the amino acid sequence of $Ala_{134}$ to $Ser_{321}$ of Formula I, starting from the plasmid pCL-2.
Figure 5:
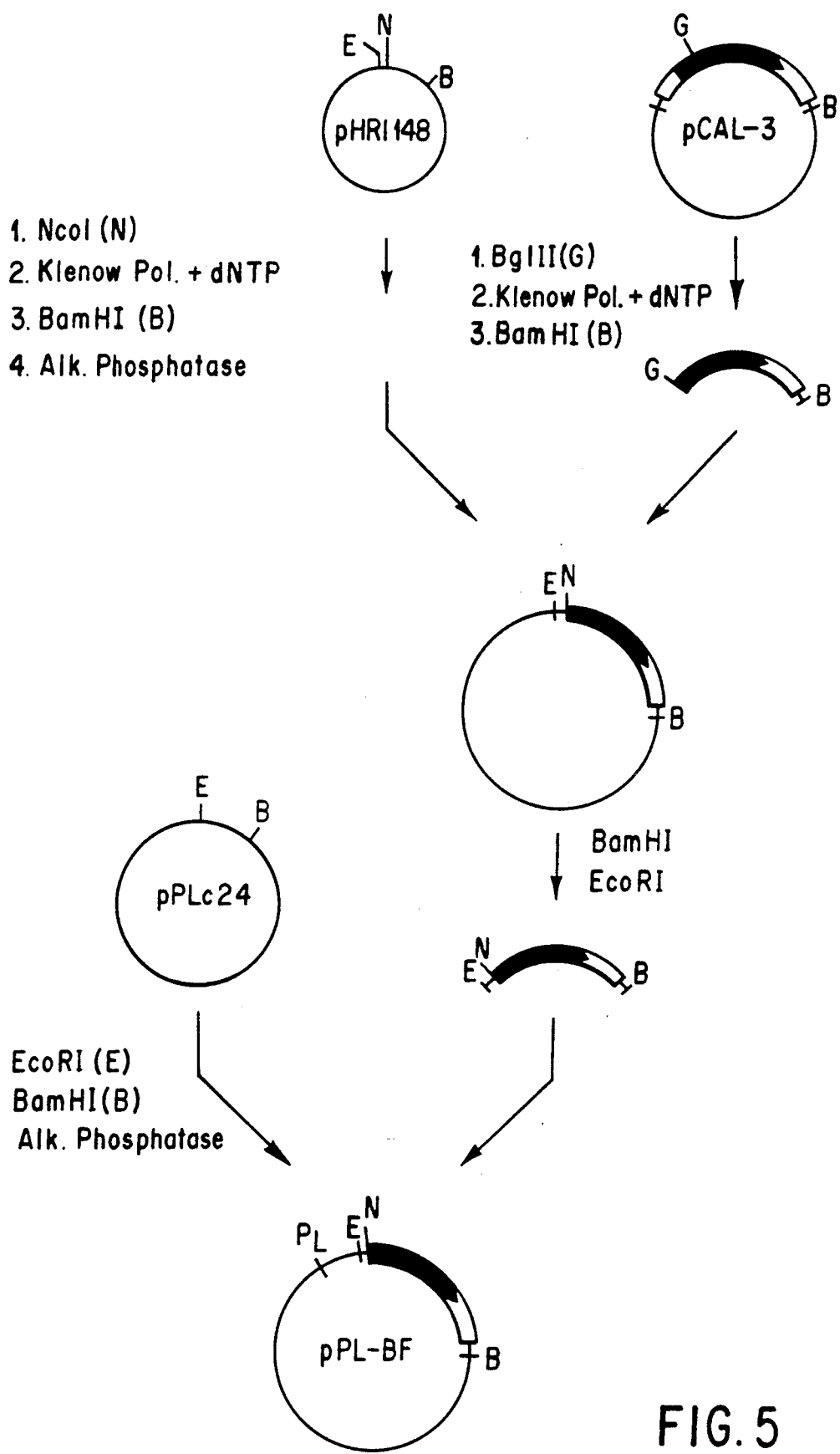
FIG. 5: The construction of plasmid pBL-BF for expression of IgE-BF in E. coli W3110 and HB101. Expressed are amino acids 119 to 321 under the $P_L$ promoter of phage λ.
Figure 6:
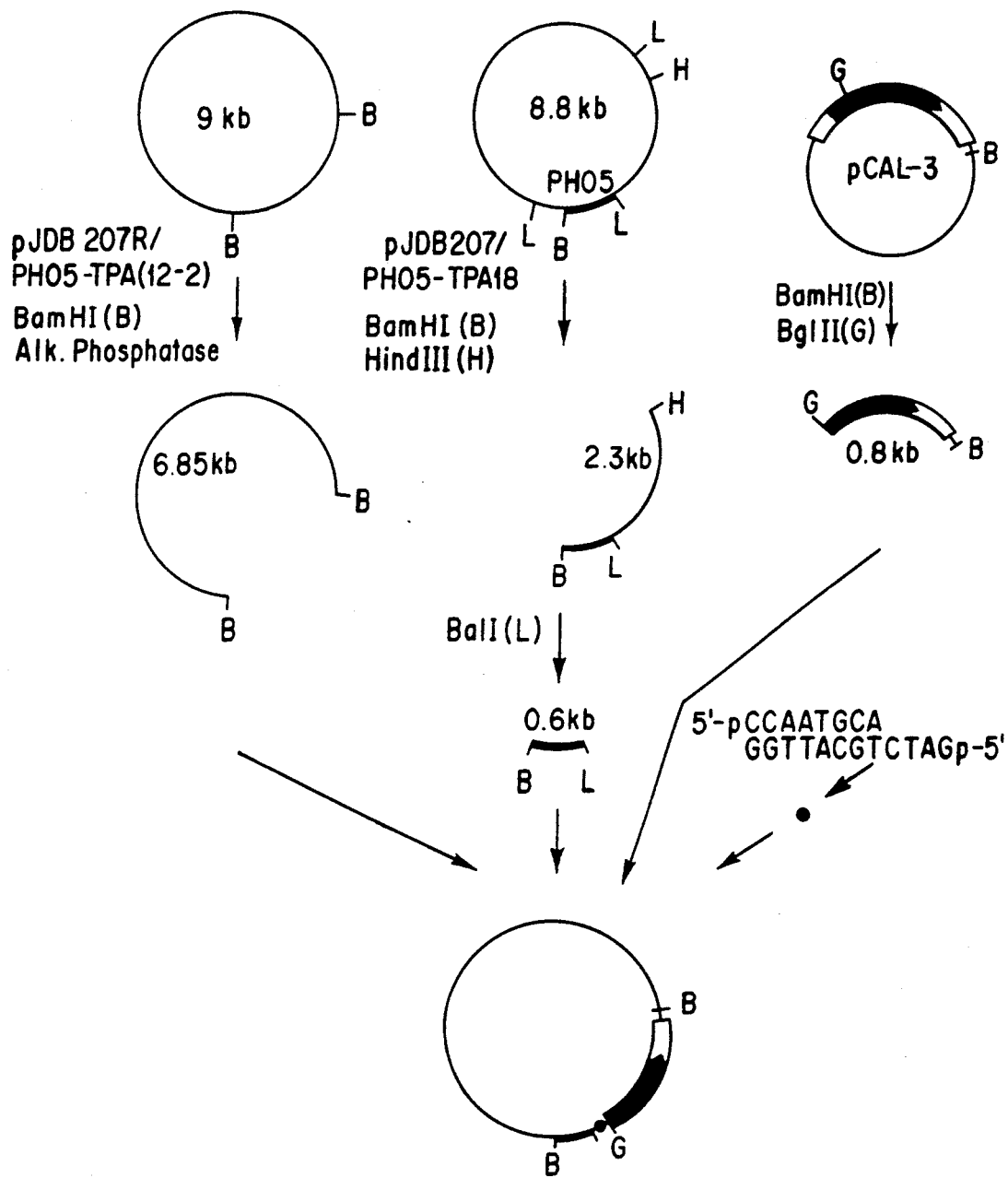
FIG. 6: The construction of plasmid pJDB207R/PHO5-BF for expression of IgE-BF in Saccharomyces cerevisiae. Expressed are amino acids 119 to 321 under the PHO5 promoter.
Figure 7:
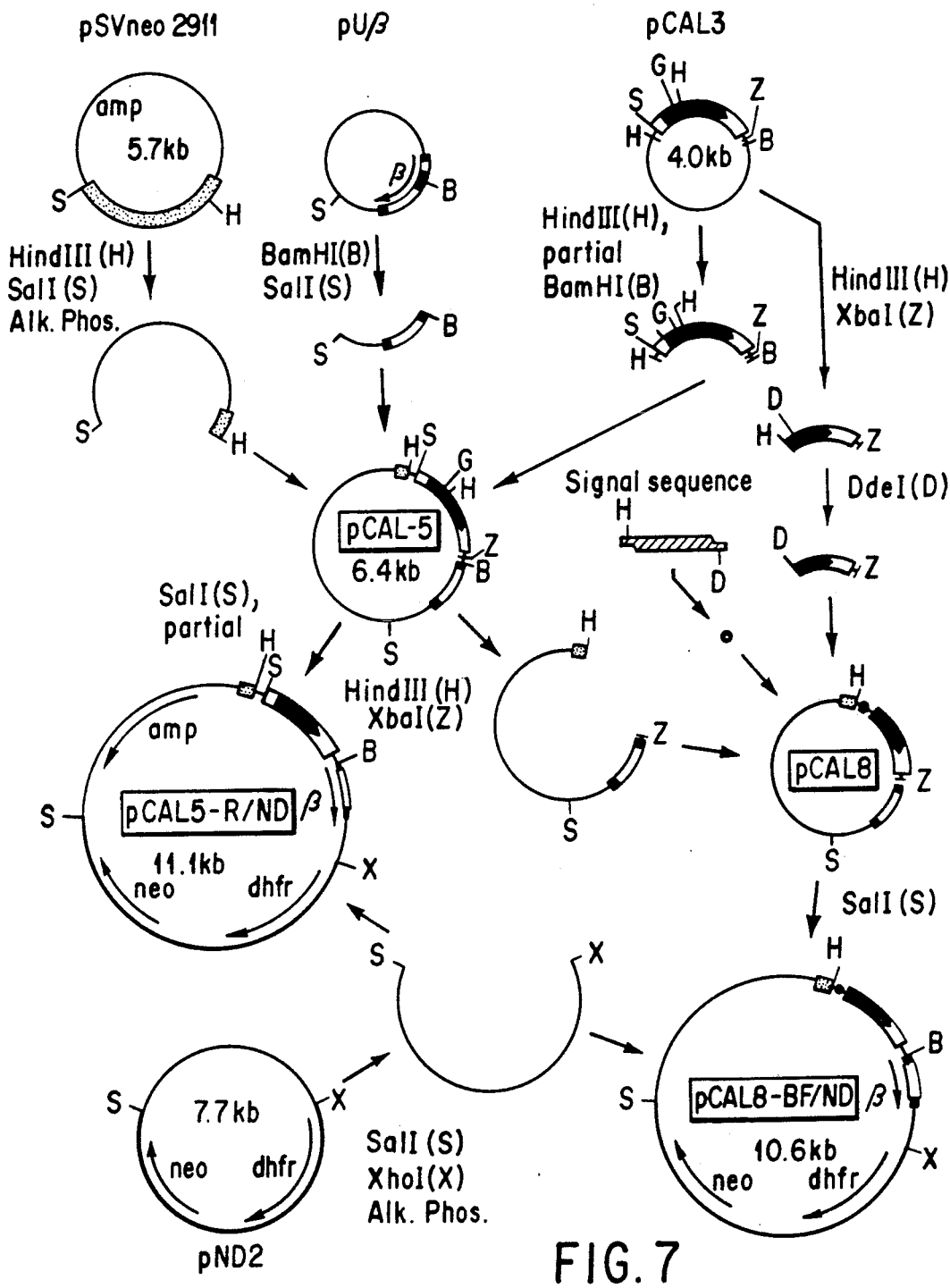
FIG. 7: The construction of plasmids pCAL5-R/ND and pCAL8-BF/ND for the expression of membrane bound IgE receptor or secreted IgE-BF, respectively, in cultured mammalian cells (Chinese hamster ovary cells).
Figure 8:
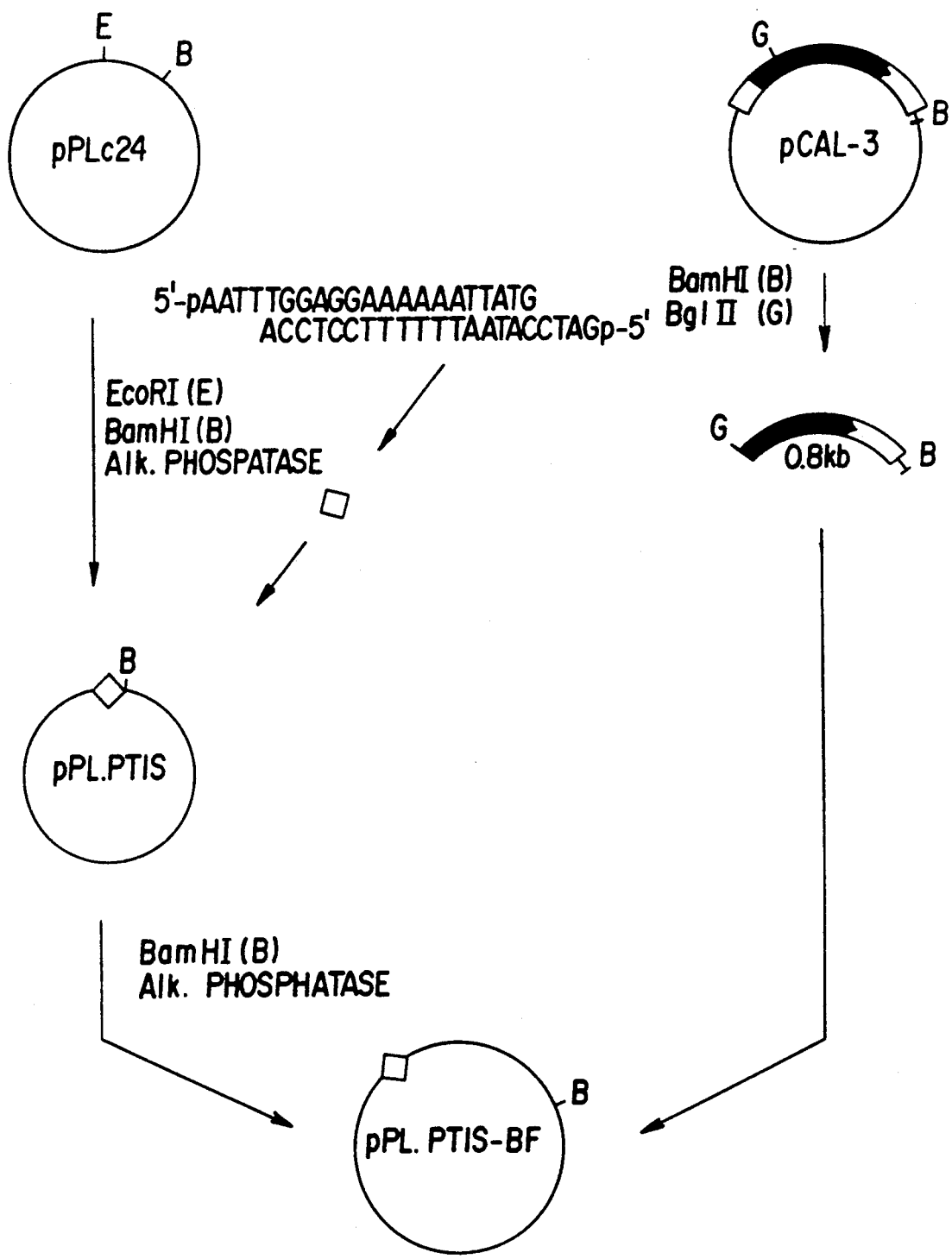
FIG. 8: The construction of plasmid pPL.PTIS-BF for transformation and expression of IgE-BF in E. coli.

|   |   |   |
|---|---|---|
| G, | H, | and R | are shown.

FIG. 11: DNA-Sequence (formula III) of pCL-1 cDNA insert. The coding region for a derivative of the polypeptide of formula (I) is marked by the amino acid symbols the meanings of which are given in the legend of FIG. 9. Restriction sites

|   |   |   |
|---|---|---|
| G, | H, | and R | are shown.

| Legend: Restriction enzymes | |
|---|---|
| A = HaeII | G = BglIII |
| B = BamHI | H = HindIII |
| C = HincII | N = NcoI |
| E = Eco RI | P = PstI |
|  | R = RsaI |

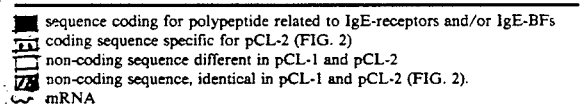

Deposition of Microorganism

The Escherichia coli HB101/pCL-2 containing the plasmid pCL-2 was deposited on July 30, 1986 at the Deutsche Sammlung für Mikroorganismen, Grisebachstrasse 8, D-3400 Göttingen, under Accession number DSM 3807.

REFERENCES

1. Maniatis et al., Molecular Cloning, A Laboratory Manual, Cold Spring Harbor Laboratory (1982)
2. Okayama and Berg, Molecular and Cellular Biology 2, 161–170 (1982)

3. Heidecker and Messing, Nucleic Acids Research 11, 4891–4906 (1983)
4. S. A. Narang et al., Anal. Biochem. 121, 365 (1982)
5. K. L. Agarwal et al., Angew. Chem. 84, 489 (1972)
6. C. B. Reese, Tetrahedron 34, 3143 (1972)
6a. R. L. Letsinger et al., J. Am. Chem. Soc. 98, 3655 (1976)
7. Khorana et al., J. Biol. Chem. 251, 565 (1976)
8. S. A. Narang, Tetrahedron 39, 3 (1983)
9. Chang et al., Nature, 275: 615 (1978)
10. Goedell et al., Nature, 281: 544 (1979)
11. Goedell et al., Nucleic Acid Res., 8: 4057 (1980)
12. Siebenlist et al., Cell 20: 269 (1980)
13. J. Gharayeb et al., The EMBO Journal, Vol. 3, 2437–2442 (1984)
14. Stinchomb et al., Nature, 282: 39 (1979)
14a. Kingsman et al., Gene, 7: 141 (1979)
15. Tschemper et al., Gene, 10, 157 (1980)
16. Melton, D. A. et al. (1984) Nucleic Acids Research 12, 7035–7056
17. M. Sarfati et al., Immunology, 1984, 53, 197–205
18. J. B. Gurdon, The control of gene expression in animal development, Clarenton Press, Oxford, 1974
19. F. C. Greenwood et al., Biochem. J. 89, 114 (1963)
20. B. Seed, Nucleic Acids Res. 10, 1799–1810 (1982)
21. F. Sanger et al., Proc. Nat. Acad. Sci. USA 74, 5463–5467

What is claimed is:

1. A method for the preparation of a transformed eucaryotic or procaryotic host capable of expressing a polypeptide having the amino acid sequence of the formula (I) shown in FIG. 9, or a fragment thereof having at least 10 up to 320 successive amino acids, exhibiting IgE-binding activity and optionally expressed in the form of a fusion protein; comprising the steps of
   1. preparing a DNA coding for a polypeptide having the amino acid sequence of the formula (I) shown in FIG. 9, or a fragment thereof,
   2. incorporating the obtained DNA into an appropriate eucaryotic or procaryotic plasmid, cosmid or phage vector,
   3. transforming an appropriate host selected from procaryotic or eucaryotic cells with the obtained hybrid vector, and
   4. selecting the transformed host from untransformed hosts.

2. A method according to claim 1 for the preparation of a transformed host capable of expressing a protein encoded by the amino acid sequence of the formula (I) shown in FIG. 9.

3. A method according to claim 1 for the preparation of a transformed host capable of expressing the fragment of a protein having the amino acid sequence of formula (I) shown in FIG. 9 consisting of the amino acid sequence from amino acid 119–321.

4. A method according to claim 1 for the preparation of a transformed host capable of expressing the fragment of a protein having the amino acid sequence of formula (I) shown in FIG. 9 consisting of the amino acid sequence from amino acid 134–321.

5. A method according to claim 1 for the preparation of a transformed host capable of expressing the fragment of a protein having the amino acid sequence of formula (I) shown in FIG. 9 consisting of the amino acid sequence from amino acid 148 or 150 to 321.

6. A method according to claim 5 for the preparation of a transformed host capable of expressing the fragment of a protein having the amino acid sequence of formula (I) shown in FIG. 9 consisting of the amino acid sequence from amino acid 148 to 321.

7. A method according to claim 5 for the preparation of a transformed host capable of expressing the fragment of a protein having the amino acid sequence of formula (I) shown in FIG. 9 consisting of the amino acid sequence from amino acid 150 to 321.

8. A method according to claim 1 for the preparation of a transformed *E. coli* host.

9. A method according to claim 1 for the preparation of a transformed *E. coli* host harboring a gene for the $\lambda cI_{857}$ repressor and plasmid pPL-BF.

10. A method according to claim 1 for the preparation of a transformed *E. coli* host harboring a gene for the $\lambda cI_{857}$ repressor and plasmid pPLPTIS-BF.

11. A method according to claim 1 for the preparation of a transformed *Saccharomyces cerevisiae* host.

12. A method according to claim 11, wherein said transformed host is a transformed *Saccharomyces cerevisiae* host harboring plasmid pJDB 207 R/PHO5-BF.

13. A method according to claim 1 wherein said transformed host is a transformed CHO cell line.

14. A method according to claim 13 wherein said transformed CHO cell line is harboring plasmid pCAL5-R/ND.

15. A method according to claim 13 wherein said transformed CHO cell line is harboring plasmid pCAL8-BF/ND.

* * * * *